United States Patent
Kaushansky et al.

(10) Patent No.: US 10,207,728 B2
(45) Date of Patent: Feb. 19, 2019

(54) PORTABLE AND MODULAR TRANSPORTATION UNIT WITH IMPROVED TRANSPORT CAPABILITIES

(75) Inventors: Yefim Kaushansky, North Haledon, NJ (US); Zina Kaushansky, legal representative, North Haledon, NJ (US); Edmund Pacenka, Westwood, NJ (US); Robert Hamilton, Bergenfield, NJ (US)

(73) Assignee: MAQUET CARDIOVASCULAR LLC, Wayne, NJ (US)

(*) Notice: Subject to any disclaimer, the term of this patent is extended or adjusted under 35 U.S.C. 154(b) by 0 days.

(21) Appl. No.: 13/470,205

(22) Filed: May 11, 2012

(65) Prior Publication Data

US 2012/0289765 A1 Nov. 15, 2012

Related U.S. Application Data

(60) Provisional application No. 61/486,227, filed on May 13, 2011.

(51) Int. Cl.
| | |
|---|---|
| *A61N 1/362* | (2006.01) |
| *B62B 3/02* | (2006.01) |
| *A61M 1/10* | (2006.01) |
| *B62B 5/06* | (2006.01) |
| *A61M 1/12* | (2006.01) |

(52) U.S. Cl.
CPC ............... *B62B 3/02* (2013.01); *A61M 1/106* (2013.01); *A61M 1/107* (2013.01); *A61M 1/1072* (2013.01); *A61M 1/1074* (2014.02); *A61M 1/125* (2014.02); *A61M 2209/084* (2013.01); *B62B 5/067* (2013.01); *B62B 2202/56* (2013.01); *B62B 2202/90* (2013.01); *B62B 2205/145* (2013.01); *B62B 2206/02* (2013.01)

(58) Field of Classification Search
CPC .......... A61M 1/1072; A61M 2209/084; B62B 2205/145; B62B 2206/02; B62B 3/02; B62B 5/067
USPC ........................................................... 600/18
See application file for complete search history.

(56) References Cited

U.S. PATENT DOCUMENTS

| | | | |
|---|---|---|---|
| 2,535,762 A | 12/1950 | Tapp | |
| 2,577,290 A * | 12/1951 | Underwood | 280/646 |
| 2,857,725 A | 10/1958 | Canfield | |
| 3,749,193 A | 7/1973 | Blase | |

(Continued)

FOREIGN PATENT DOCUMENTS

| | | |
|---|---|---|
| CA | 2284417 A1 | 3/2001 |
| EP | 1238884 A1 | 9/2002 |
| FR | 1001698 A | 2/1952 |

OTHER PUBLICATIONS

International Search Report and Written Opinion for PCT/US2012/037640 dated Mar. 8, 2013.

(Continued)

*Primary Examiner* — Lindsey G Wehrheim
(74) *Attorney, Agent, or Firm* — Wesley Scott Ashton; Kirk Swenson

(57) ABSTRACT

A medical device, such as an intra-aortic balloon pump or carrier with an extendable wheel track and handle configured to be removably carried and integrated with a cart. The wheel track is configured to extend upon extension of the handle and to return to its original position upon retraction of the handle.

25 Claims, 21 Drawing Sheets

(56) References Cited

U.S. PATENT DOCUMENTS

| | | | |
|---|---|---|---|
| 4,175,264 A | | 11/1979 | Kaushansky |
| 4,834,409 A | * | 5/1989 | Kramer .................. 180/209 |
| 4,957,121 A | | 9/1990 | Icenogle et al. |
| 5,116,289 A | | 5/1992 | Pond et al. |
| 5,228,706 A | | 7/1993 | Boville |
| 5,230,408 A | | 7/1993 | Sadow |
| 5,249,438 A | | 10/1993 | Rhaney et al. |
| 5,263,727 A | | 11/1993 | Libit et al. |
| 5,337,845 A | * | 8/1994 | Foster et al. ................ 180/11 |
| 5,373,708 A | | 12/1994 | Dumoulin |
| 5,505,471 A | | 4/1996 | Cheng |
| 5,549,317 A | | 8/1996 | Dunkle |
| 5,752,661 A | * | 5/1998 | Lewis ............. B05B 9/0861 |
| | | | 222/175 |
| 6,098,405 A | | 8/2000 | Miyata et al. |
| 6,296,605 B1 | | 10/2001 | Michelman et al. |
| 6,299,183 B1 | * | 10/2001 | Kaneko ................ 280/47.26 |
| 6,343,674 B1 | | 2/2002 | Sexsmith |
| 6,374,933 B1 | | 4/2002 | Ruppert et al. |
| 6,405,842 B1 | | 6/2002 | Tsai |
| 6,412,796 B1 | | 7/2002 | Kroniger |
| 6,488,029 B1 | | 12/2002 | Hood et al. |
| 6,497,311 B2 | | 12/2002 | Tiramani et al. |
| 6,802,515 B2 | | 10/2004 | Sorenson |
| 7,066,311 B2 | | 6/2006 | O'Shea |
| 7,614,628 B2 | | 11/2009 | O'Connor |
| 7,669,862 B2 | | 3/2010 | Kamara et al. |
| 2003/0055309 A1 | * | 3/2003 | Kaushansky et al. .......... 600/18 |
| 2004/0000457 A1 | | 1/2004 | Sanford Schwentke |
| 2004/0163910 A1 | | 8/2004 | Lee |
| 2005/0161916 A1 | | 7/2005 | Taylor |
| 2007/0039794 A1 | | 2/2007 | Hwang |
| 2007/0216131 A1 | | 9/2007 | Potappel |
| 2010/0052293 A1 | | 3/2010 | Brooks et al. |
| 2010/0209095 A1 | | 8/2010 | DeSorbo |

OTHER PUBLICATIONS

Product Brochure—CS300 IABP—Product Features—2009 Publication—Maquet Cardiovascular LLC. U.S.A.
Product Brochure—CS100 IABP—Intelligent Counterpulsation—2010 Publication—Maquet Cardiovascular LLC. U.S.A.
Operators Guide—The CS100/CS100i Abbreviated Operators Guide—2009 Publication—Maquet Cardiovascular LLC. U.S.A.
Operators Guide—Datascope Abbreviated Operators Guide for the System 97 Intra-Aortic Balloon Pump—Published prior to 2009—Datascope Corp. U.S.A.
Brochure—Sensation and CS300 IABP System Smaller Meets Faster—Published in 2009—Maquet Cardiovascular LLC. U.S.A.
CS100/CS100i Abbreviated Operator's Guide—2009—Maquet Cardiovascular LLC.—USA.
CS100 Universal Transport System (UTS)—Sell Sheet—prior to 2008—Datascope Corp.—USA.
Transport Protocols for Patients on an Intra-Aortic Balloon Pump—2002—Datascope Corp.—U.S.A.
Quick Reference Guide—IAB Insertion / CS300 Operation—Maquet Cardiovascular LLC—Dec. 2011.
2010 Product Catalog—Cardiac Assist—Maquet Cardiovascular LLC—2009—U.S.A.
Unpublished pending U.S. Appl. No. 13/089,128, filed Apr. 18, 2011. First named inventor is Yefim Kaushansky.
Unpublished pending U.S. Appl. No. 29/389,514, filed Apr. 12, 2011. First named inventor is Aidan Hyde.
Unpublished pending U.S. Appl. No. 29/385,398, filed Feb. 14, 2011. First named inventor is Ralph J. Ebler.
Abbreviated Operation and Troubleshooting Guide—Arrow AutoCat2 WAVE IAB Abbreviated Operation and Troubleshooting Guide—2005—Arrow International, Inc.
Troubleshooting Brochure—Troubleshooting Beyond the Basics—Arrow Intra-Aortic Balloon Pump—1999—Arrow International, Inc.
Educational Material—AutoCAT2 Series Intra-Aortic Balloon Pump—Timing, Triggering, and Troubleshooting—2005—Arrow International, Inc. U.S.A.
Brochure/Flyer—Feature Comparison—Arrow AutoCAT2 Series—2006—Arrow International, Inc. U.S.A.
Educational Materials—ACAT1 Plus Intra-Aortic Balloon Pump—Timing, Triggering, and Troubleshooting—2005—Arrow International, Inc. U.S.A.
Brochure—Changing Disposable Helium Tank—2005—Arrow International, Inc. U.S.A.
Examination Report issued in counterpart AU Application No. 2017213552, dated Nov. 2, 2018.

* cited by examiner

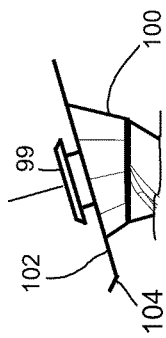
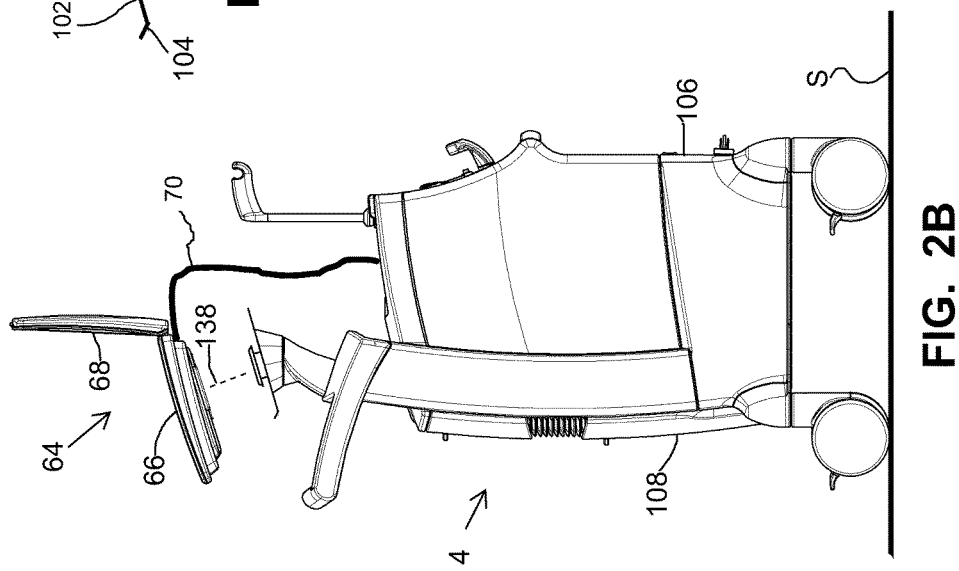
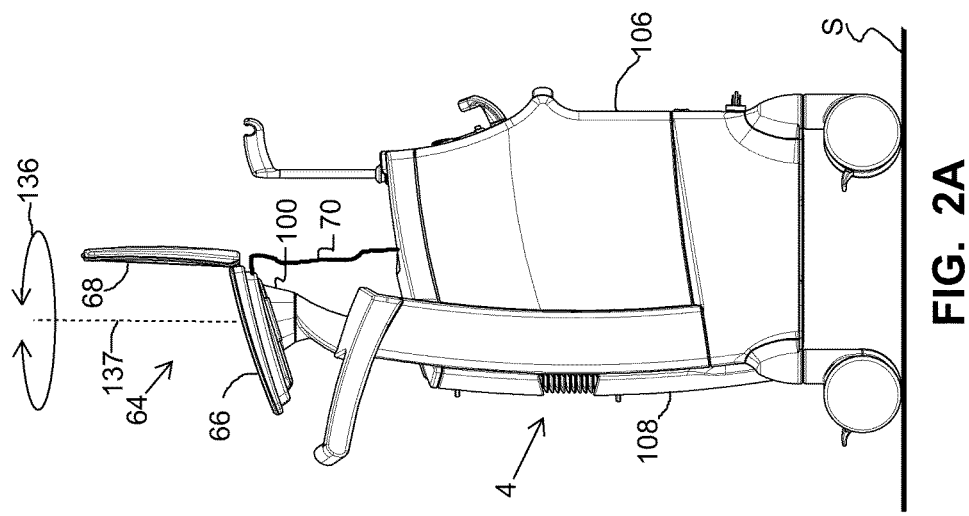

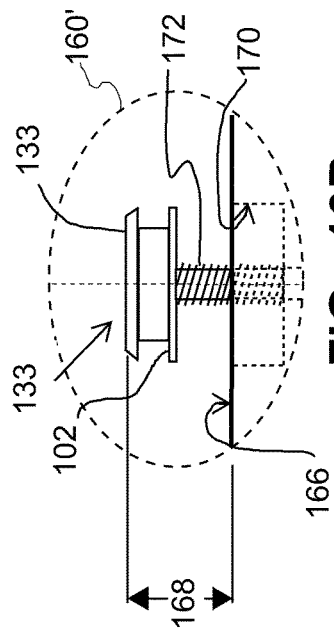
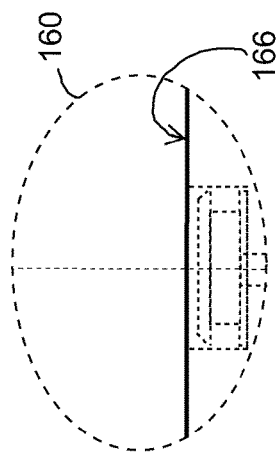
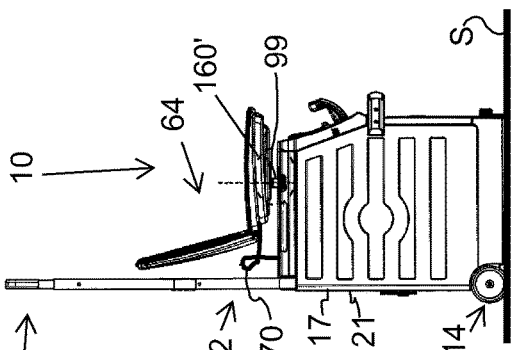
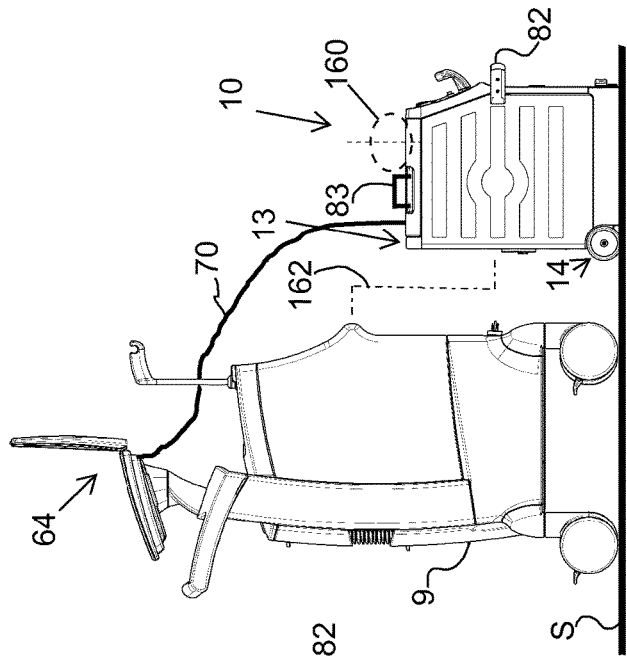
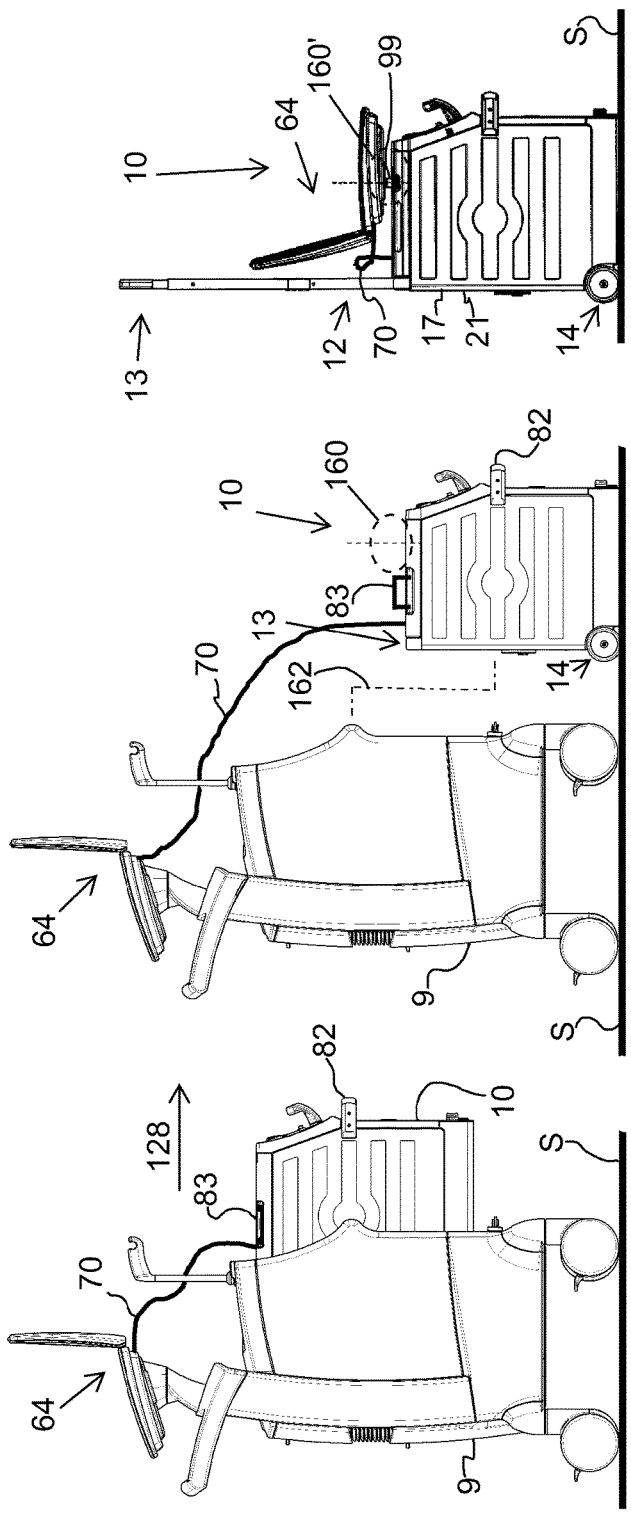

PORTABLE AND MODULAR TRANSPORTATION UNIT WITH IMPROVED TRANSPORT CAPABILITIES

This application claims benefit of priority to U.S. Provisional Patent Application No. 61/486,227, filed May 13, 2011, the entire disclosure of which is incorporated herein by reference in its entirety.

BACKGROUND OF THE INVENTION

Field of the Invention

The present invention generally relates to a modular and portable carrier unit adaptable to a plurality of usage environments. An example embodiment of the present invention relates to a portable medical device, such as an intra-aortic balloon pump with an extendable wheel system.

Description of Related Art

Intra-aortic balloon pumps (IABPs) are used to provide pneumatic assistance to a failing or weakened heart. This therapy is provided in different medical facilities, environments, and situations specific to the location, access, and condition of a patient. IABPs are often needed to transition patients between such different environments or facilities, and therefore are desired to be selectively adaptable to each and transportable. Current IABPs are typically wheeled and include a handle for moving the IABP together with the patient within hospital or trauma environments. A need exists for an IABP system specifically adapted to facilitate transport while a maintaining high level of functionality and usability in all of the different environments or facilities IABs are used.

SUMMARY OF THE INVENTION

A carrier according to an example embodiment of the present invention comprises a body, a wheel assembly connected to the body, a handle assembly connected to the body. The handle assembly comprising a handle movable between a first position and a second position. The wheel assembly comprising a first and second wheel, each movable between: (i) a retracted position defining a first wheel track in which the wheels are spaced apart a predetermined distance, and (ii) an extended position defining a second wheel track larger than the first in which the wheels are spaced apart a distance greater than the predetermined distance. Movement of the handle from the first position to the second position causes movement of the wheels from the retracted position to the extended position.

According to an example embodiment, movement of the handle from the second position to the first position causes relative movement of the first wheel towards the second wheel.

According to an example embodiment, movement of the handle is in a direction perpendicular to an axis through the first wheel and second wheel.

According to an example embodiment, movement of the wheels between the eaten position and the retracted position is along a common axis.

According to an example embodiment, the first and second wheels are capable of providing wheeled support to the body in both the extended and retracted positions when the body is in a tilted orientation.

According to an example embodiment, the handle assembly includes a plurality of telescoping members.

According to an example embodiment, the first wheel and second wheel when in the retracted position are disposed at least partially within recesses in the body, and in the extended position the first wheel and second wheel are disposed outside the recesses.

According to an example embodiment, each of the first wheel and second wheel is connected to a separate axle.

According to an example embodiment, the axles are constrained to linear movement.

According to an example embodiment, the handle assembly includes a plurality of telescoping members. Each of the axles is connected to one of the telescoping members through a linkage. The first wheel and second wheel are each configured to rotate about a common axis in both the retracted and extended positions.

According to an example embodiment, the carrier is configured such that a downward or upward movement of the telescoping members cause the axles to shift laterally along the common axis in a direction perpendicular to the downward or upward movement of the handle. The axles move towards each other along the common axis when the telescoping members are moved downward and move away from each other when the telescoping members are moved upward.

According to an example embodiment, the body of the carrier is integral to an intra-aortic balloon pump.

According to an example embodiment, the intra-aortic balloon pump comprises a pump, a frame enclosing the pump, a monitor, and at least two power supplies. Each of the at least two power supplies configured to independently power the intra-aortic balloon pump.

According to an example embodiment, the body comprises a front, a back, a top, a bottom, and two sides. Within a horizontal plane, the sides are longer than the back. The common axis of the wheel assembly is located towards or at the bottom of the body and either adjacent to or in the proximity of the back.

According to an example embodiment, the carrier is configured to stand vertically on a flat surface without the wheels engaging the surface in both the retracted and extended positions.

An intra-aortic balloon pump according to an example embodiment of the present invention includes a frame, a pump disposed within the frame, a display device, a control unit configured to control the pump, and a wheel assembly connected to the frame. The wheel assembly comprises a first and second wheel, each movable between: (i) a retracted position defining a first wheel track in which the wheels are spaced apart a predetermined distance, and (ii) an extended position defining a second wheel track larger than the first in which the wheels are spaced apart a distance greater than the predetermined distance.

According to an example embodiment, the intra-aortic balloon pump comprises a handle assembly connected to the frame. The movement of the wheels from the retracted position to the extended position is triggered by movement of at least a portion of the handle assembly from a first position to a second position.

According to an example embodiment, the handle assembly includes a plurality of telescoping members.

According to an example embodiment, the first wheel and second wheel when in the retracted position are disposed at least partially within recesses in the frame, and in the extended position are disposed outside the recesses.

According to an example embodiment, each of the first wheel and second wheel is connected to a separate axle.

According to an example embodiment, the intra-aortic balloon pump comprises a handle assembly connected to the frame. The handle assembly includes a plurality of telescoping members. Each of the axles is connected to one of the telescoping members through a linkage. The first wheel and second wheel are each configured to rotate about a common axis in both the retracted and extended positions.

According to an example embodiment, a downward or upward movement of the telescoping members cause the axles to shift laterally along the common axis in a direction perpendicular to the downward or upward movement of the telescoping members. Further, the axles move towards each other along the common axis when the telescoping members are moved downward and move away from each other when the telescoping members are moved upward.

According to an example embodiment, the intra-aortic balloon pump comprises at least two power supplies. Each of the at least two power supplies is configured to independently power the intra-aortic balloon pump.

An example method of the present invention for enhancing the stability of an intra-aortic balloon pump during transport, comprises the steps of moving the first wheel and the second wheel of the intra-aortic balloon pump wheel assembly from (i) a retracted position defining a first wheel track in which the wheels are spaced apart a predetermined distance, to (ii) an extended position defining a second wheel track larger than the first in which the wheels are spaced apart a distance greater than the predetermined distance.

An example method according to the present invention may further include the step of moving at least a portion of the handle assembly of the intra-aortic balloon pump from a first position to a second position so as to trigger the movement of the wheels from the retracted position to the extended position.

According to an example embodiment, in the retracted position the first wheel at least partially resides in a first recess in the frame and the second wheel at least partially resides in a second recess in the frame. Further, in the extended position the first wheel resides outside the first recess and the second wheel resides outside the second recess.

A modular portable intra-aortic balloon pump according to an example embodiment of the present invention comprises a wheeled cart with at least one caster, and a pump unit. The pump unit includes a frame, a pump disposed within the frame, a display device in electronic communication with the pump unit, a control unit configured to control the pump, and a wheel assembly connected to the frame. The wheel assembly includes a first and second wheel, each movable between: (i) a retracted position defining a first wheel track in which the wheels are spaced apart a predetermined distance, and (ii) an extended position defining a second wheel track larger than the first in which the wheels are spaced apart a distance greater than the predetermined distance. The wheeled cart is configured to removably and securely house and transport the pump unit using the at least one caster but without use of the first and second wheels. The pump unit is also transportable independently when removed from the wheeled cart via the first and second wheels.

According to an example embodiment, the cart has a cavity with a cavity entrance, and the pump unit is configured to be removably received into the cavity through the cavity entrance.

According to an example embodiment, the pump unit cannot fit through the cavity entrance when the first and second wheels are each in the extended position.

According to an example embodiment, the cavity entrance is horizontal to the cavity. Further, a release mechanism having a release actuator on at least one of the cart or pump unit is configured to establish releasable securement of the pump unit with respect to the cavity.

According to an example embodiment, the display device is a monitor comprising a mounting interface. The cart has a first monitor mount and the pump unit has a second monitor mount. The mounting interface on the monitor configured to reversibly engage and secure to both the first mount and the second mount one at a time.

According to an example embodiment, the pump unit includes a recess and the second monitor mount is configured to move within the recess between a retracted position and an extended position. When in the extended position, the second monitor mount projects from an external surface of the pump unit more so than when in the retracted position.

According to an example embodiment, the second monitor mount is confined to the retracted position when the pump unit is fully disposed within the housing cavity.

According to an example embodiment, the pump unit comprises a body with one or more recesses. The first and second wheels at least partially disposed within the one or more recesses when in their retracted position and lie outside the one or more recesses when in their extended position.

According to an example embodiment, the modular portable intra-aortic balloon pump further comprises a handle assembly connected to the pump unit and configured to telescopically move between a first handle position to a second handle position.

According to an example embodiment, movement of the handle assembly from the first position towards the second position causes relative movement of the first wheel towards and second wheel.

According to an example embodiment, the modular portable intra-aortic balloon pump further comprises a first power supply on the cart and a second power supply on the pump unit. When the pump unit is disposed within the cavity the first power supply is used to deliver power to the pump unit, and when the pump unit is removed from the cavity the second power supply is used to power the pump unit.

According to an example embodiment, the modular portable intra-aortic balloon pump further comprises a third power supply on the pump unit, and both the second power supply and the third power supply are configured to independently power the pump unit.

A modular portable intra-aortic balloon pump according to an example embodiment of the present invention comprises a wheeled cart and a wheeled pump unit removably mounted on or in the cart. The pump unit includes a frame, a pump disposed within the frame, a control unit configured to control the pump, a display device in electronic communication with the pump unit, and a wheel assembly connected to the frame. The cart includes a first power source used to power the pump unit when the pump unit is mounted on or in the cart. The pump unit comprises a second power source used to power the pump unit when the pump unit is removed from the cart or when the pump unit is on or in the cart but the first power source is not functional.

According to an example embodiment, the pump comprises a first and second wheel, each movable between: (i) a retracted position defining a first wheel track in which the wheels are spaced apart a predetermined distance, and (ii) an extended position defining a second wheel track larger than the first in which the wheels are spaced apart a distance greater than the predetermined distance. The cart is configured to removably and securely house and transport the pump unit using at least one caster connected to the cart but without use of the first and second wheels. The pump unit is also transportable independent and removed from the cart via the first and second wheels.

According to an example embodiment, the portable intra-aortic balloon pump further comprises a third power source on the pump unit. Both the second power source and the third power source are capable of powering the pump unit independently when the pump unit is removed from the cart.

According to an example embodiment, the display device is configured to display information and also to serve as an input device.

According to an example embodiment, the portable intra-aortic balloon pump further comprises a first gas reservoir connected to the cart and a second gas reservoir connected to the pump unit. The second gas reservoir is configured and used to provide gas to the pump unit during operation of the pump unit. The first gas reservoir is configured and used to refresh gas in the second gas reservoir.

According to an example embodiment, the pump unit is configured to connect to a third gas reservoir to refill the second gas reservoir when the pump unit is removed from the cart.

A modular portable intra-aortic balloon pump according to an example embodiment of the present invention comprises a wheeled cart, and a wheeled pump unit removably mounted on or in the cart. The pump unit includes a frame, a pump disposed within the frame, a control unit configured to control the pump, a display device in electronic communication with the pump unit, and a wheel assembly connected to the frame. A first gas reservoir is connected to the cart and a second gas reservoir is connected to the pump unit. The second gas reservoir is configured and used to provide gas to the pump unit during operation of the pump unit. The first gas reservoir is configured and used to refresh gas in the second gas reservoir.

According to an example embodiment, the pump unit is configured to connect to a third gas reservoir to refill the second gas reservoir when the pump unit is removed from the cart.

A modular portable intra-aortic balloon pump according to an example embodiment of the present invention comprises a wheeled cart and a wheeled pump unit removably mounted on or in the cart. The pump unit is configured to connect to a catheter based device. The pump unit includes a frame, a pump disposed within the frame, and a first processor configured to control the pump and to collect patient data from the catheter based device. The pump unit is directly connected to a display device via a cable. The display device includes one or more second processors configured to process the patient data and display the patient data on the display device. The cable being of sufficient length to span a first distance between the pump unit and the display device when the display device is mounted on the pump unit and also to span a second distance larger distance between the pump unit and the display device when the display device is mounted on the cart.

An example method for operating a modular medical system including a pump unit connected to a cart comprises the step of removing the wheeled pump unit from a housing cavity in the cart while each of first and second extendable wheels on the pump are in a retracted position.

According to an example method, prior to or during the step of removing, the method comprises releasing a reversible latching mechanism between the cart and the pump unit.

According to an example method, after removing the pump unit, a pump unit monitor support is extended from the pump unit and a monitor is removed from a cart-based monitor support and connected to the pump unit monitor support.

According to an example method, the first and second extendable wheels are extended to change a wheel track between the first and second extendable wheels. This extension may be achieved remotely from the first and second extendable wheels.

A portable intra-aortic balloon pump according to one example embodiment of the invention includes a compressor, a pneumatic isolator and a fill system. The pneumatic isolator is operatively associated with the compressor and includes a membrane that separates the pneumatic isolator into a drive side and a patient side. Movement of the membrane provides for inflation and deflation of an intra-aortic balloon when intra-aortic balloon is in fluid communication with the intra-aortic balloon pump. The fill system supplies pressurized gas to the patient side and includes a fill manifold. The fill manifold includes an internal reservoir, one or more valves for controlling gas supply to the patient side, a pressurized gas source, and one or more valves for allowing fluid communication between the internal reservoir and the pressurized gas source to fill the internal reservoir.

According to an example embodiment, the pressurized gas source is external to the intra-aortic balloon pump.

According to an example embodiment, the internal reservoir has an internal volume of about 50 cubic centimeters to about 400 cubic centimeters.

According to an example embodiment, the internal reservoir is internally mounted in the intra-aortic balloon pump.

According to an example embodiment, the internal reservoir is a permanently integrated component of the intra-aortic balloon pump.

According to an example embodiment, the internal reservoir is free of a valve integral thereto.

According to an example embodiment, the internal reservoir is a tank.

According to an example embodiment, the gas is helium and the pressurized gas source is a replaceable helium tank including a valve integral thereto.

According to an example embodiment, a connector is positioned on an exterior surface of the intra-aortic balloon pump for connecting to the pressurized gas source.

According to an example embodiment, the pressurized gas source is a helium tank mounted to a cart, the intra-aortic balloon pump is configured to reversibly dock to the cart, pneumatic connectors are located on both the cart and intra-aortic balloon pump to establish a pneumatic coupling therebetween and to further allow for the helium tank mounted to the cart to refill the internal reservoir with helium.

According to an example embodiment, the invention further includes a tank frame for protecting and supporting a portable tank, wherein the gas is helium and the secondary pressurized gas source is the replaceable tank mounted to the tank frame.

A portable intra-aortic balloon pump system according to one example embodiment the invention includes an intra-aortic balloon pump for inflating and deflating an intra-aortic balloon catheter when connected to the intra-aortic balloon pump; a first tank connected to the intra-aortic balloon pump for supplying gas to the intra-aortic balloon pump to enable inflation and deflation of the intra-aortic balloon catheter; and a recharge tank connectable to the first tank to fill the first tank.

According to an example embodiment, the first tank is integral with the intra-aortic balloon pump.

According to an example embodiment, the system comprises a wheeled cart. The intra-aortic balloon pump and the first tank are mounted on the wheeled cart.

According to an example embodiment, the recharge tank is pneumatically connectable to the first tank.

According to an example embodiment, the wheeled cart includes a pneumatic fitting engaging the intra-aortic balloon pump to allow for recharging of the first tank.

According to an example embodiment, the recharge tank is mounted on the wheeled cart or a portable holder of the system.

According to an example embodiment, the recharge tank is mounted on the portable holder, wherein the portable holder includes a base connected to a frame for securing the recharge tank.

According to an example embodiment, the portable holder further includes a strap for supporting the recharge tank.

According to an example embodiment, the first tank is connected to a patient side of an intra-aortic balloon pump.

According to an example embodiment, the first tank is smaller than the recharge tank.

According to an example embodiment, the system includes a fill manifold capable of connecting the recharge tank to the first tank.

According to an example embodiment, the recharge tank has an integral valve.

According to an example embodiment, the wheeled cart includes a cord that draws power from a first power source external to the system to supply power to the intra-aortic balloon pump.

According to an example embodiment, the cord is retractable relative to the wheeled cart.

According to an example embodiment, the intra-aortic balloon pump is removably mounted to the wheeled cart and includes a first power source and second power source to supply power to the intra-aortic balloon pump.

According to an example embodiment, the first and second power sources are selected from the group consisting of a battery and an AC to DC converter.

According to an example embodiment, the first power source is a battery and wherein the second power source is an AC to DC converter.

A method for maintaining a volume of gas in an intra-aortic balloon pump system according to one example embodiment of the invention includes an intra-aortic balloon pump system that includes an intra-aortic balloon pump for inflating and deflating an intra-aortic balloon catheter when connected to the intra-aortic balloon pump; a first tank connected to the intra-aortic balloon pump for supplying gas to the intra-aortic balloon pump to enable inflation and deflation of the intra-aortic balloon catheter; and a recharge tank connectable to the to the first tank. The method involves the step of supplying gas from the recharge tank to the first tank.

According to an example method, the gas is supplied to the first tank to recharge the first tank after gas is leaked from the first tank.

According to an example method, the method further involves sensing when gas falls below a predetermined threshold in at least one of the intra-aortic balloon catheter and the first tank and using the recharge tank to replenish the gas in at least one of the intra-aortic balloon catheter and the first tank.

Reference throughout this specification to "an embodiment" or "an exemplary embodiment" or the like means that a particular feature, structure, or characteristic described in connection with the embodiment is included in at least one embodiment of the present invention. Thus, the appearances of these phrases in various places throughout this specification are not necessarily all referring to the same embodiment. Furthermore, the particular features, structures, or characteristics may be combined in any suitable manner in one or more embodiments.

Reference throughout this specification to a "carrier" means any body, object, device, assembly, etc. that can be integral to or supported by a wheeled device or system. A carrier may also be a wheeled and portable medical system, such as an intra-aortic balloon pump.

Reference throughout this specification to a "pump unit" refers to a medical system comprising a pump. An example of a "pump unit" is an intra-aortic balloon pump.

Reference throughout this specification to "wheel track" means the side-to-side horizontal distance spanning two wheels or wheel groupings. The "wheel track" of an object is generally perpendicular to the direction the object's normal travel path. "Wheel base" means generally the front-to-back horizontal distance of a front and rear set of wheels, wheel pairs, or wheel groupings. As for a wheel grouping or wheel pair, the wheel base shall be considered the distance between the mid-point of the wheel pairs or groupings, wherein each wheel, wheel pair, or wheel grouping is capable of supporting a load.

Additionally, for purposes of the description hereinafter, the words "upper," "lower," "right," "left," "vertical," "horizontal," "top," "bottom," "lateral," "longitudinal," "axial," and like terms, if used, shall relate to the invention, as it is oriented in the Figures. It is to be understood that the invention may assume many alternative variations and embodiments except where expressly specified to the contrary. It is also to be understood that the specific devices and embodiments illustrated in the accompanying drawings and described herein are simply example embodiments of the invention.

Additionally, the word "processor" can be used interchangeably with "controller" and CPU and control unit.

Example embodiments of the present invention are described in more detail below with reference to the Figures. The foregoing description and examples have been set forth as mere illustrations and are not intended to be limiting. Each of the disclosed aspects and embodiments may be considered individually or in combination with other aspects, embodiments, and variations thereof. The steps of the methods described herein are not confined to any particular order of performance.

BRIEF DESCRIPTION OF THE DRAWINGS

FIGS. 2A and 2B are side elevation views of the IABP of FIG. 1 shown without the intra-aortic balloon catheter and with a monitor attached in FIG. 2A and detached in FIG. 2B.

FIG. 3 is a magnified partial view of the monitor support, structure in FIG. 2B.

FIG. 7 is a side elevation view of the IABP of FIG. 5.

FIG. 8 is a side elevation view of the IABP of FIG. 5 with the pump unit fully removed from the cart and placed on a ground surface.

FIG. 9 is a side elevation view of the pump unit in a stand-alone configuration.

FIG. 10A is a magnified partial view taken about dashed border 160 in FIG. 8.

FIG. 10B is a magnified partial view taken about dashed border 160' in FIG. 9.

DETAILED DESCRIPTION OF THE PRESENT INVENTION

Figure 1:
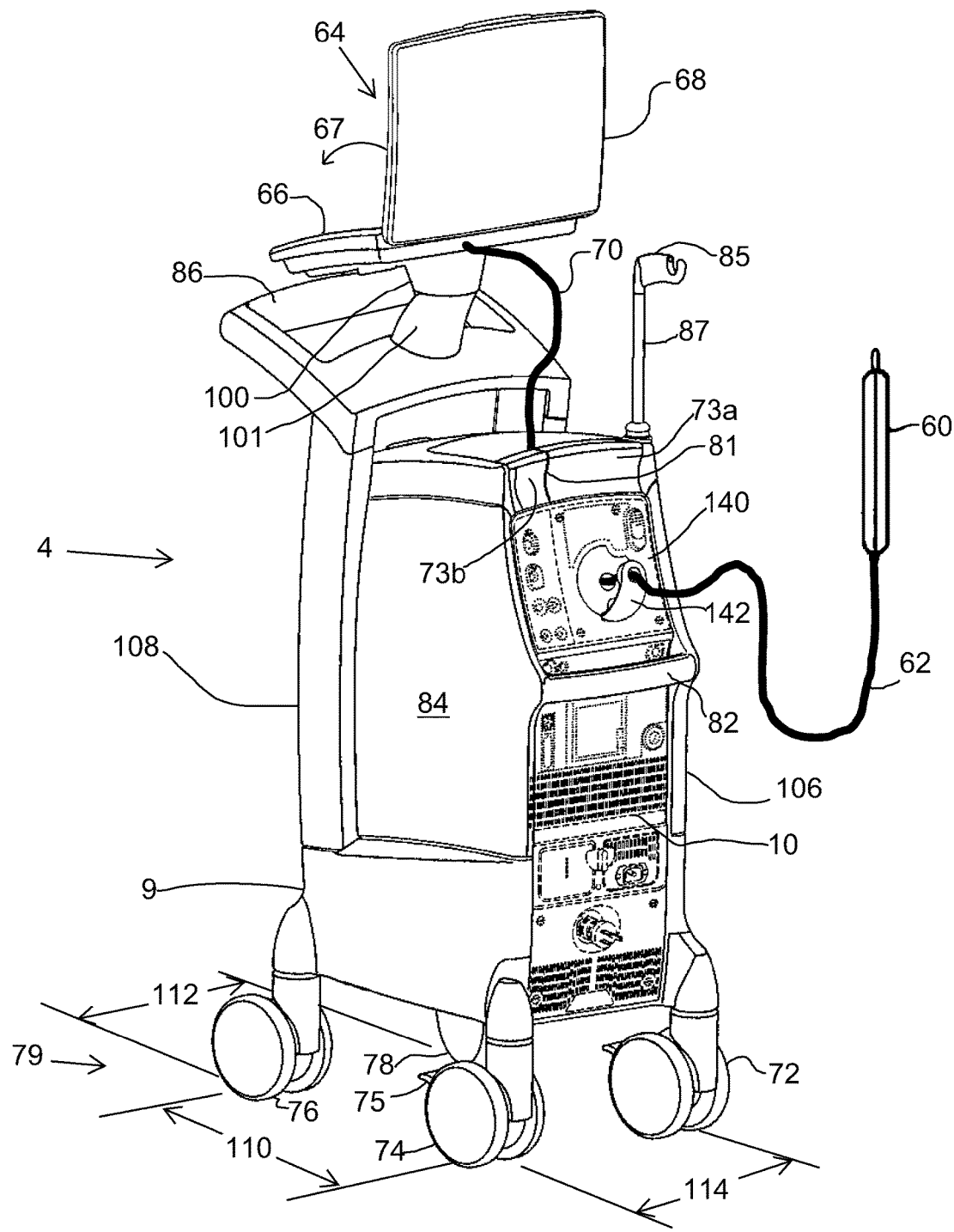
FIG. 1 is a rear perspective view of an IABP in a cart-based configuration according to an exemplary embodiment of the present invention.

FIG. 1 illustrates a perspective view of a multi-format modular medical system 4 configured, for example, to monitor and/or provide therapy to patients. As illustrated in FIG. 1, modular medical system 4 is a multi-format intra-aortic balloon pump ("IABP") with a transportable pump unit 10 removably docked to a cart 9 and communicating with a monitor 64. However, the pump unit 10 can be replaced with another type of medical device requiring, for example, a transport mode with access to a monitor, such as an ultra-sound machine or a circulatory support device.

Figure 6:
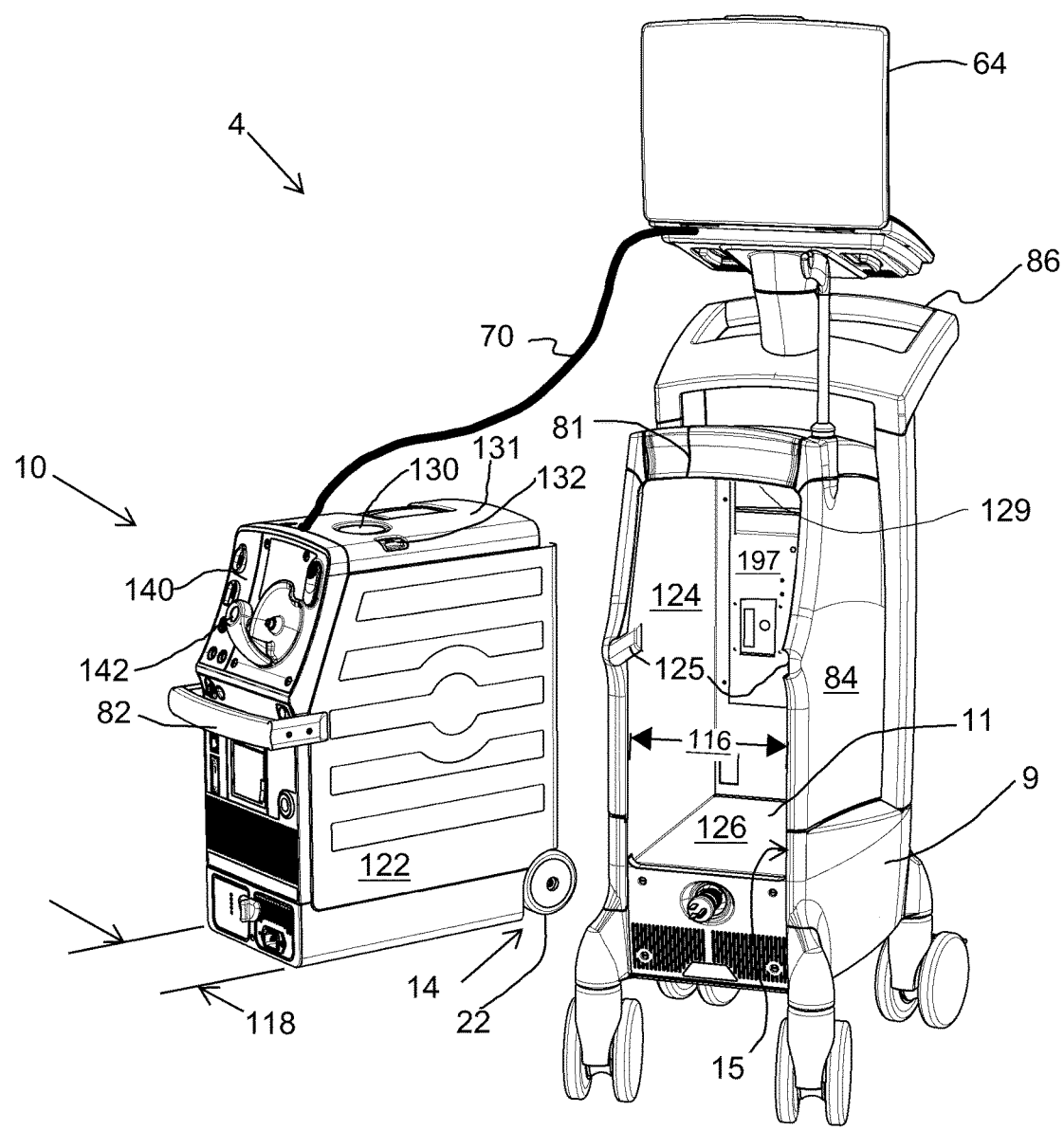
FIG. 6 is a rear perspective view of the IABP of FIG. 4 with the pump unit fully removed from the cart.
Figure 11:
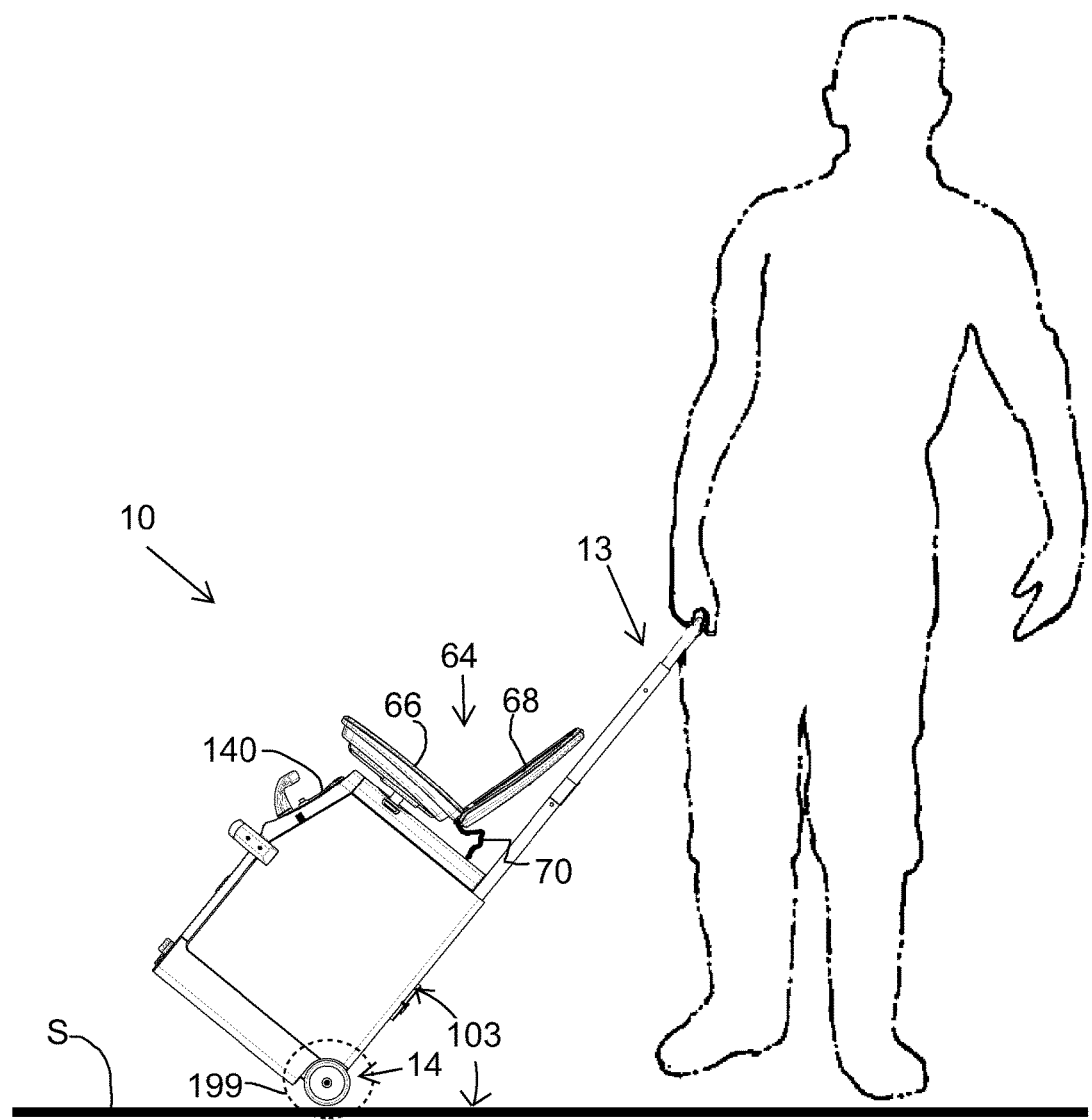
FIG. 11 is tilted elevation view of the pump unit in tow by an operator.

The cart 9 has a front side 108, a rear side 106, and a wheel arrangement 79. The medical system 4 may be used, e.g., patient bedside in a hospital, with the pump unit 10 docked as shown in FIG. 1. The pump unit 10 may also be removed from the cart 9 for transport and used to deliver therapy alongside of and/or independent of the cart 9, as illustrated in FIGS. 6, 9, and 11. As detailed below, and illustrated in FIGS. 13A, 13B, and 14, a wheel assembly 14 of the pump unit 10 may be expanded prior to transport to improve tracking and stability for the pump unit 10.

Figure 24:
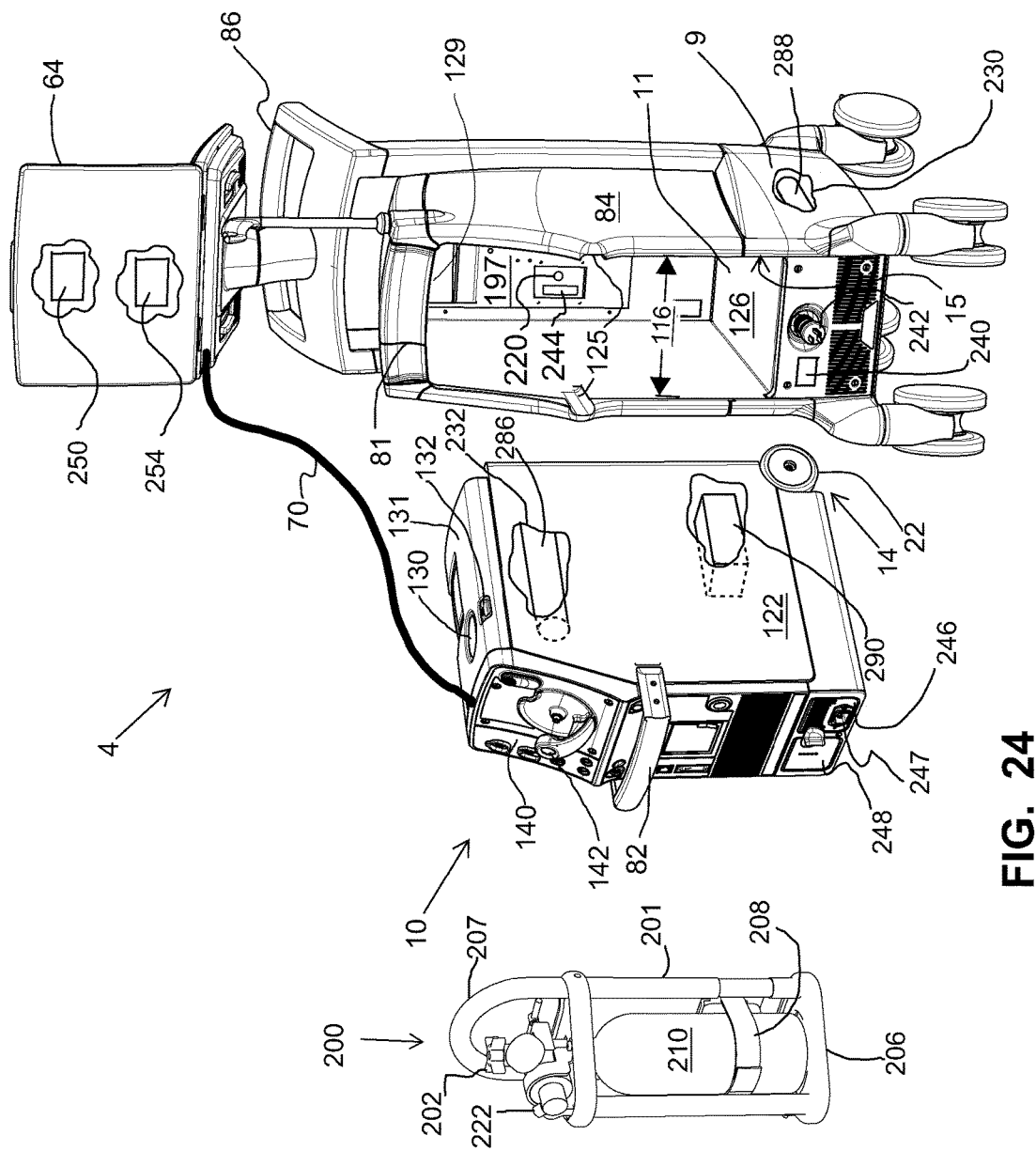
FIG. 24 is a perspective view of an example embodiment of a medical pump system according to the present invention.

As recognized by one skilled in the art, IABPs are used to inflate and deflate an intra-aortic balloon 60 on a distal end of a balloon catheter 62. The balloon catheter 62 is inserted into a blood vessel of a patient and used to support the patient's heart. As detailed in U.S. Pat. No. 6,241,706, herein incorporated by reference in its entirety, the pump unit 10 includes multiple components (not all shown), such as a pump 290 (as shown in FIG. 24) (also referred to as a compressor), a control unit (250,252), a monitor 64 with an operator input interface 66 and display 68, a patient connection interface panel 140, and a power supply 240. The monitor 64 and the pump unit 10 communicate through an electronic interface such as a wire 70. The modular medical system 4 also includes a drip bag holder 85 supported by a shaft 87 and configured to hold an infusion bag (not shown). The interface panel 140 may be used to connect to patient electrocardiogram (ECG) leads, while the display 68 on monitor 64 is intended for relaying patient information to the IABP operator. Operators may control and calibrate the pump unit 10 through input interface 66. The display 68 may optionally be a fixed unit or a collapsible assembly capable of folding along the path of are 67.

Because medical system 4 is commonly used in a hospital setting, it includes cart 9 configured for movement on generally flat floors. An operator may move or reposition the modular medical system 4 within a hospital, for example, by using handle 82 located on the rear side 106, or handle 86 located on the front side 108.

Swivel or universal wheel arrangement 79 attached to the bottom or base of the cart 9 facilitates movement of cart 9. Wheel arrangement 79 comprises a plurality of swivel wheels (72, 74, 76, and 78) (also referred to as wheel sets or casters) located at the corners of the base of the modular medical system 4. The wheel sets (72, 74, 76, and 78) are configured to lock through a lock release arm 75 to prevent unintended rolling. Wheel arrangement 79 includes a wheelbase 110 between front and rear wheel sets 74 and 76, while a front wheel track 112 and rear wheel track 114 spans the distances between the midpoints of wheel sets 74, 78 and 76, 72 respectively.

The medical system 4 is modular and configurable for use in non-hospital settings or in transfers to or between hospitals. For example, the pump unit 10 may be removed from cart 9 and used as a portable stand-alone IABP device independent of the larger cart 9. The smaller footprint, lighter weight, and greater portability of the pump unit 10, as compared to the medical system 4 as a whole, add convenience for ambulatory helicopter crews and healthcare practitioners when transporting patients and their medical equipment, for example, between a hospital and non-hospital setting.

As illustrated in FIGS. 2A, 2B and 3, monitor 64 is reversibly attached to a monitor adapter 99, which may be integral with a cart-based monitor support 100 configured for complete or partial rotation about an axis 136. FIG. 2B shows monitor 64 removed and detached from the monitor adapter 99, the details of which are more specifically detailed in partial view FIG. 3. As illustrated in FIG. 3, the monitor adapter 99 extends upwards from a monitor support surface 102 on the monitor support 100. The monitor support 100 optionally may have a mechanical boss 104 or protrusion that prevents monitor 64 from rotating about the axis 138 of monitor adapter 99. As illustrated in FIG. 2A, monitor support 100 including monitor 64 is rotatable about axis 136. The monitor adapter 99 removably snaps into a recess (not shown) on a bottom surface of the monitor 64.

Figure 4:
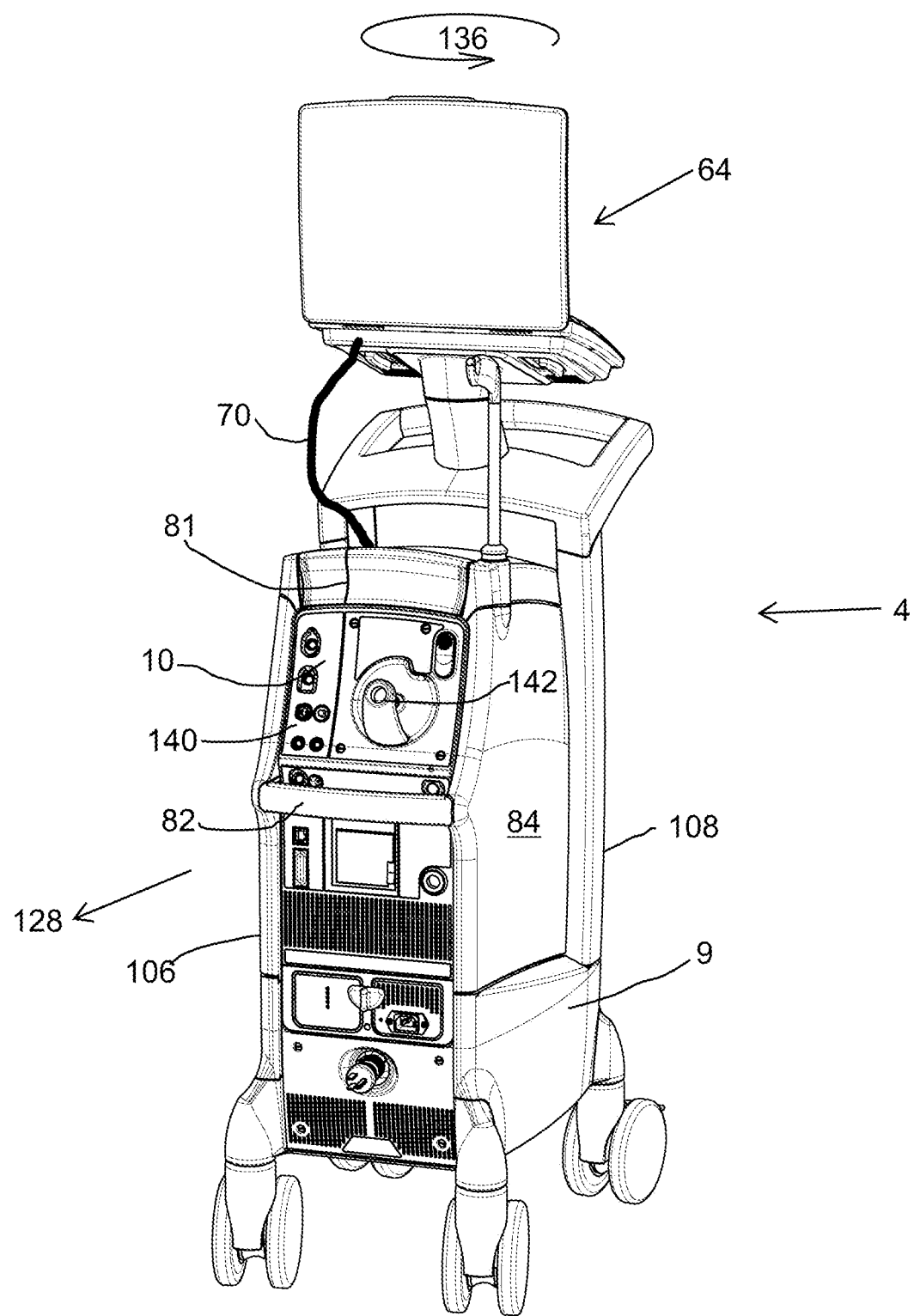
FIG. 4 is a rear perspective view of the IABP of FIG. 4 shown without the intra-aortic balloon catheter.

FIG. 4 is a rear perspective view of the medical system 4 with the pump unit 10 stored in cavity 11 (shown in FIG. 6) within the cart 9. The cart 9 has an aspect ratio similar to that of pump unit 10 so that the pump unit 10 blends into the cart 9 when inside cavity 11. Pump unit 10 has a smaller size and slimmer aspect ratio than cart 9 so that pump unit 10 may slide horizontally into and out of a cavity 11 of cart 9. The pump unit 10 has a handle 82 used to assist with insertion and removal from cart 9.

As can be seen in FIG. 6, cavity 11 has a width 116 sufficient to accommodate a minor width 118 of pump unit 10. Cavity 11 further includes a bottom surface 126, an inner sidewall 124, and an upper inner surface or sidewall 129. Cavity 11 is sized and dimensioned to accommodate with minimal clearance pump unit 10, such that a side wall 122 of pump unit 10 may be slidingly engaged with cavity 11 to help resist side-to-side movement and stability. Handle 82 is attached to the pump unit 10, extends outward, and is slidingly received into handle pockets 125 within the cavity 11, thereby providing additional stability and support to the pump unit 10. The outer surface of the handle 82 is contiguous with the outer surfaces 84 of the cart 9 when the pump unit 10 is housed in cavity 11, as shown in FIG. 4.

Figure 5:
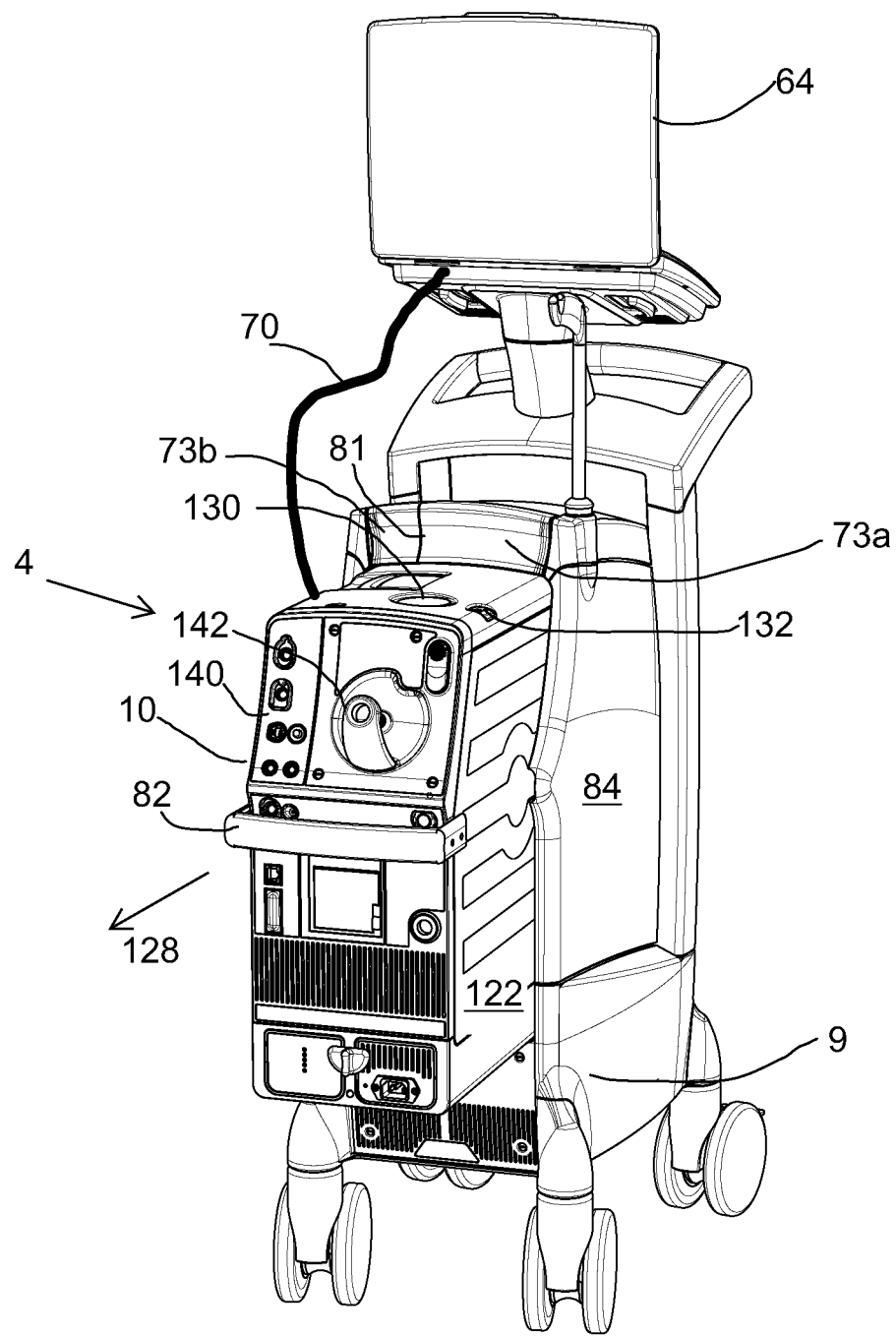
FIG. 5 is a perspective view of the IABP of FIG. 4 with the pump unit partially removed from the cart.

FIGS. 5 and 6 depict removal of the pump unit 10 from the cart 9. In FIG. 5, the pump unit 10 is partially slid out of cavity 11 in cart 9. In FIG. 6, the pump unit 10 is completely removed from the cart 9 but is still tethered to the monitor 64 connected to the cart 9. While pump unit 10 is partially extended from the cavity 11 of cart 9, as shown in FIG. 5, access is provided to a top portion of the pump unit 10 allowing, for example, monitor 64 to be mounted to extendable monitor mount 130. Wire 70 may be moved through a slot 81 of support surfaces 73a, 73b, which also function to provide for an additional handle. Therefore, the pump unit 10 can be removed from the cart 9 without requiring the wire 70 to be disconnected from either of the pump unit 10 or monitor 64. As shown in FIG. 6, monitor 64 remains mounted to the monitor support 100 of cart 9, but can be moved to the selectively extendable monitor mount 130 upon activation of a release mechanism 132 that can extend the monitor mount 130.

Figure 23A:
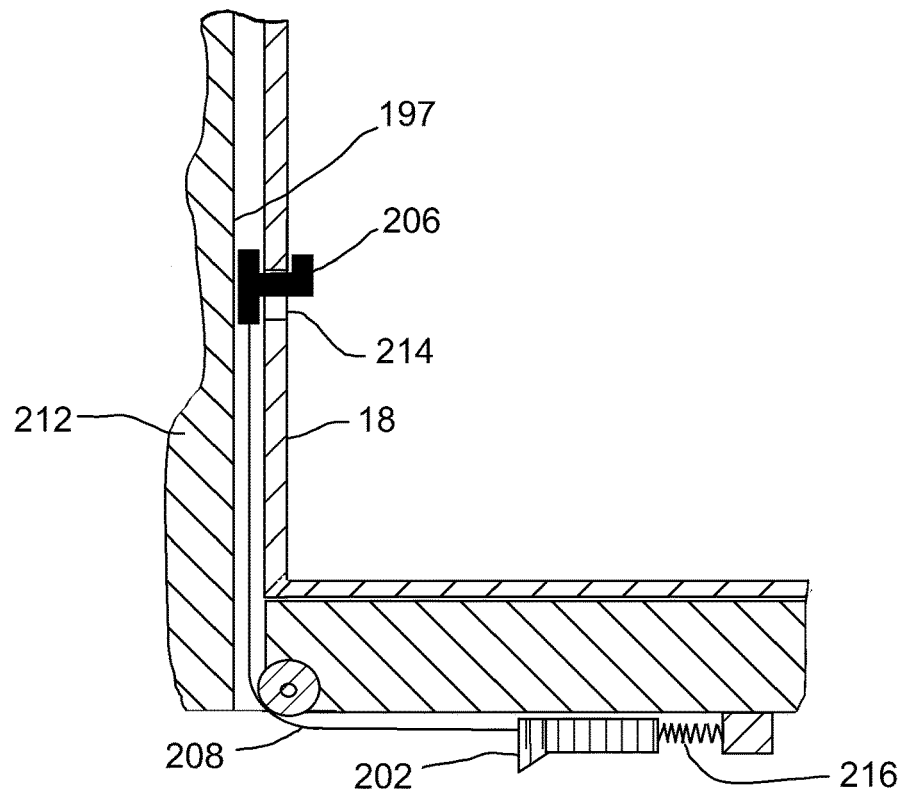
FIG. 23A is a side view of a reversible latching mechanism shown in a locked state.
Figure 23B:
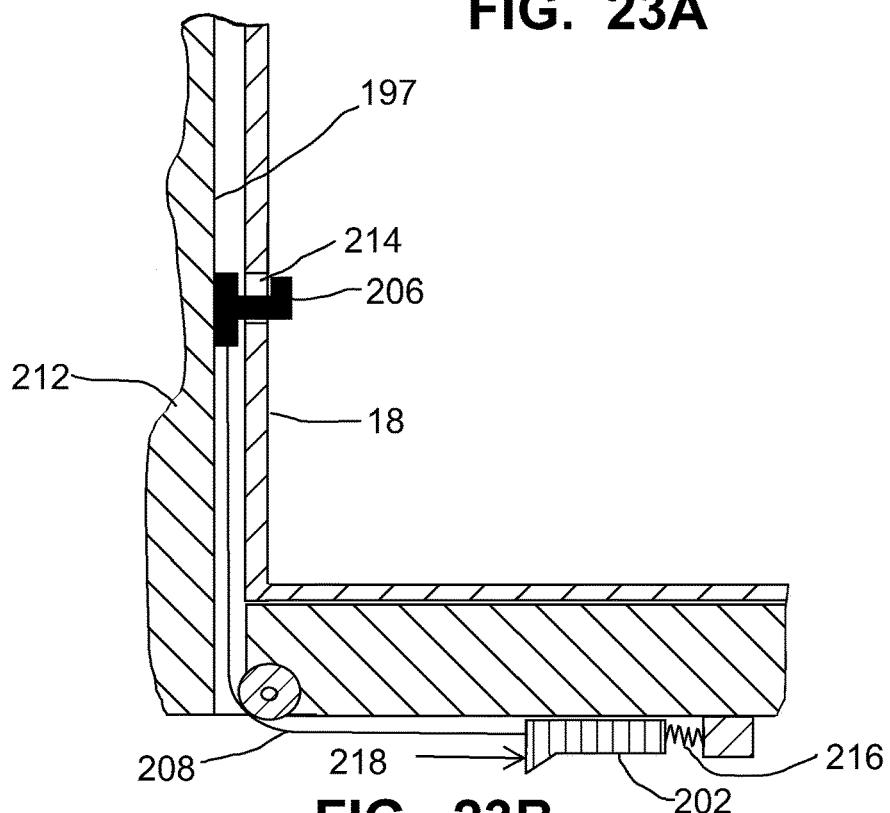
FIG. 23B is a side view of a reversible latching mechanism shown in an unlocked state.

Pump unit 10 is reversibly secured into cart 9 as follows. A reversible latching mechanism positioned on the underside of the cart 9, accessible from the rear side 106 (the same side of the cart 9 in which pump unit 10 may be removed from the cavity 11) of cart 9, locks into the cavity-facing side of pump unit 10. An exemplary schematic representation of the latching mechanism is shown in FIGS. 23A and 23B.

The latching mechanism comprises a latch 206 associated with cart 9 through the back side 197 of cavity 11. The latch 206 is connected to a handle 202 through a tether 208. The handle 202 is located on the bottom of cart 9 and is preferably spring biased to a locked position wherein latch engages back plate 18 of pump unit 10 through a latch receiving recess 214, as shown in FIG. 23A. FIG. 23B shows latch 206 downwardly shifted in recess 214 as a result of a force applied in the direction shown by arrow 218 to the handle 202 and against the bias of the spring 216. When latch 206 is disengaged from the pump unit 10, pump unit 10 may be moved from a first state (secured in cart 9) as shown in FIG. 4 to a second transition state (partially removed from cart 9) as shown in FIG. 5, to a final or third state fully removed from cart 9 shown in FIG. 6. The horizontal or lateral movement can be accomplished by an operator applied force to handle 82 in a direction depicted by arrow 128 in FIGS. 4 and 7.

FIGS. 7 through 11 are side views of the medical system 4 illustrating removal of the pump unit 10 from cart 9 starting with a cart-based configuration and transitioning to a final stand-alone configuration. Similar to FIG. 5, FIG. 7 illustrates pump unit 10 as partially removed from cart 9 through the application of a force applied to the handle 82 in the direction 128. Third handle 83 (shown lying flat and recessed in FIG. 7, and upright and extended in FIG. 8) is located on the top of pump unit 10 and enables an operator to lower the pump unit 10 to the ground or floor surface S. This is especially beneficial given that IABPs may weight more than 70 or 80 lbs (32-36 kg), and may not be easily movable, especially for petite health care providers.

Additionally shown in FIGS. 8 and 9 are features of the pump unit 10 that benefit usage for the stand-alone configuration. These features are neither accessible nor capable of being actuated while the pump unit 10 is fully docked in the cavity 11 of cart 9. Such elements include (i) an extendable monitor adapter 99, (ii) a retractable handle assembly 13, and (iii) an integral wheel assembly 14 that provides for an adjustable wheel track.

As shown in FIG. 9, monitor 64 may be attached to monitor adapter 130, best shown in FIG. 5-6 located on pump unit 10 after the monitor 64 has been removed from monitor adapter 99 of cart 9 (see FIG. 2B). FIGS. 10A and 10B are views taken about border 160 and 160' in FIGS. 8 and 9, respectively, and further illustrate monitor adapter 130 in both a recessed position below surface 166 (FIG. 10A) and an extended position above surface 166 (FIG. 10B). Monitor adapter 130 is disc-shaped (but can take on other shapes), and adapts to a conforming size and shaped structure on the bottom of monitor 64 designed specifically to removably accommodate the adapter 130. Additionally depicted in FIG. 10B is a monitor support surface 102 that provides support to the bottom of monitor 64 when positioned about the monitor adapter 130. Support surface 102 and monitor adapter 99 both are connected to a spring-loaded post assembly 172 that is configured to reversibly extend a top portion of support surface 102 to a distance 168 (greater than one inch) above surface 166 upon activation of a release mechanism 132. When moved to its recessed condition, a latch (not shown) retains the support surface 102 in it the recessed condition until actuated. In its recessed position, support surface 102 does not impede positioning of pump unit 10 into or out of cavity 11 of cart 9.

The pump unit 10, when separated from the cart 9, is designed to be operable as a standalone unit. As apparent from FIGS. 5 through 9, the pump unit 10 has a slim profile which is beneficial for docking to the cart 9. When ECG leads and catheters are connected between the patient and pump unit's panel, the slim profile enables the interface panel 140 to be placed proximate to a patient in a minimally intrusive manner. Additionally, having the interface panel 140 extending from a short or narrow side of the pump unit 10 is beneficial for the cart-based format of the IABP. However, when the pump unit 10 is transported in a tilted dolly-like manner as shown in FIG. 11, it is beneficial that the cables and catheter tubing (not shown) extending from the interface panel 140 are on a side of the pump unit 10 opposite the wheels. This prevents the cables and catheter tubing from dragging along the ground or becoming caught in the wheels of the pump unit 10 or the patient's stretcher or wheelchair. It also helps the operator avoid tripping over the lead and catheter cables and tubing.

The pump unit 10, when separated from the cart 9, is designed to operate as a standalone transportable unit using carrier 12. However, to place a wheel assembly on side of the pump unit opposite to the location of the interface panel 140 provides a challenge because the slim shape of pump unit 10 would require a small wheel track due to the need to fit within the cavity 11 of the cart 9. To improve stability during transporting of the pump unit 10 when in a stand-alone format, a carrier 12 comprising an extendable and integral wheel assembly 14 has been discovered and adaptable for usage in a manner consistent with the embodiments disclosed herein. Located on the pump unit 10 towards the side opposite the interface panel 140 is a carrier 12 with an integral wheel assembly 14 for selective transport of the pump unit 10 when in a stand-alone configuration. The carrier 12 is connected or integral to a frame 17 or chassis of the pump unit 10, e.g., along its back side 21, and includes a retractable handle assembly 13 and integral wheel assembly 14. The handle assembly 13 can be used to tow pump unit 10 in a stand-alone configuration, similar to a transport dolly or upright wheeled luggage. In other embodiments, the wheel assembly may be non-integral or reversibly connected to the frame 17 or chassis.

Figures 15, 16:
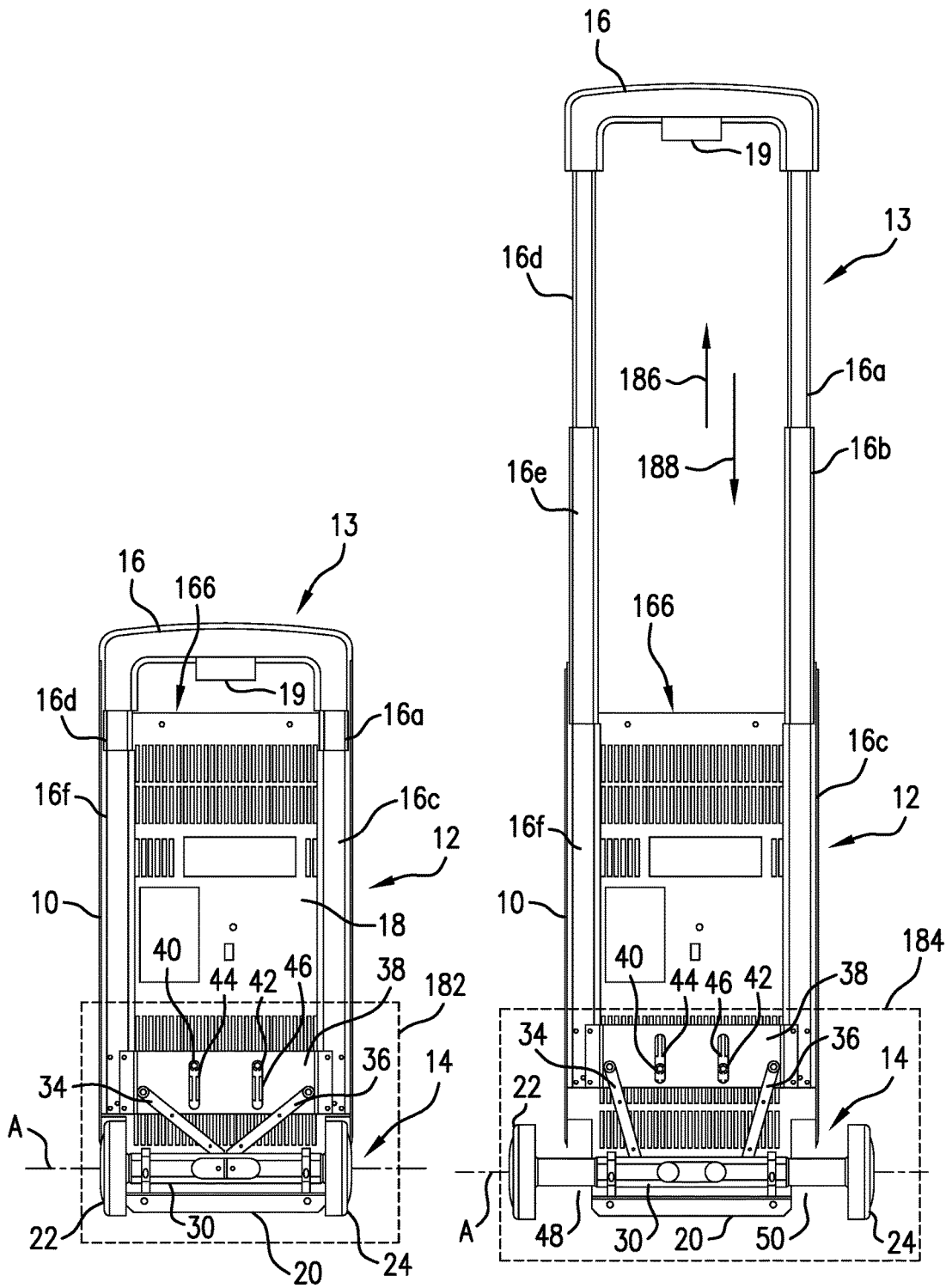
FIG. 15 is a rear view of a carrier portion of an exemplary embodiment of the present invention with both the wheels and handle in a closed or contracted arrangement.
FIG. 16 is a rear view of a carrier portion of an exemplary embodiment of the present invention with both the wheels and handle in an extended or expanded arrangement.
Figure 18:
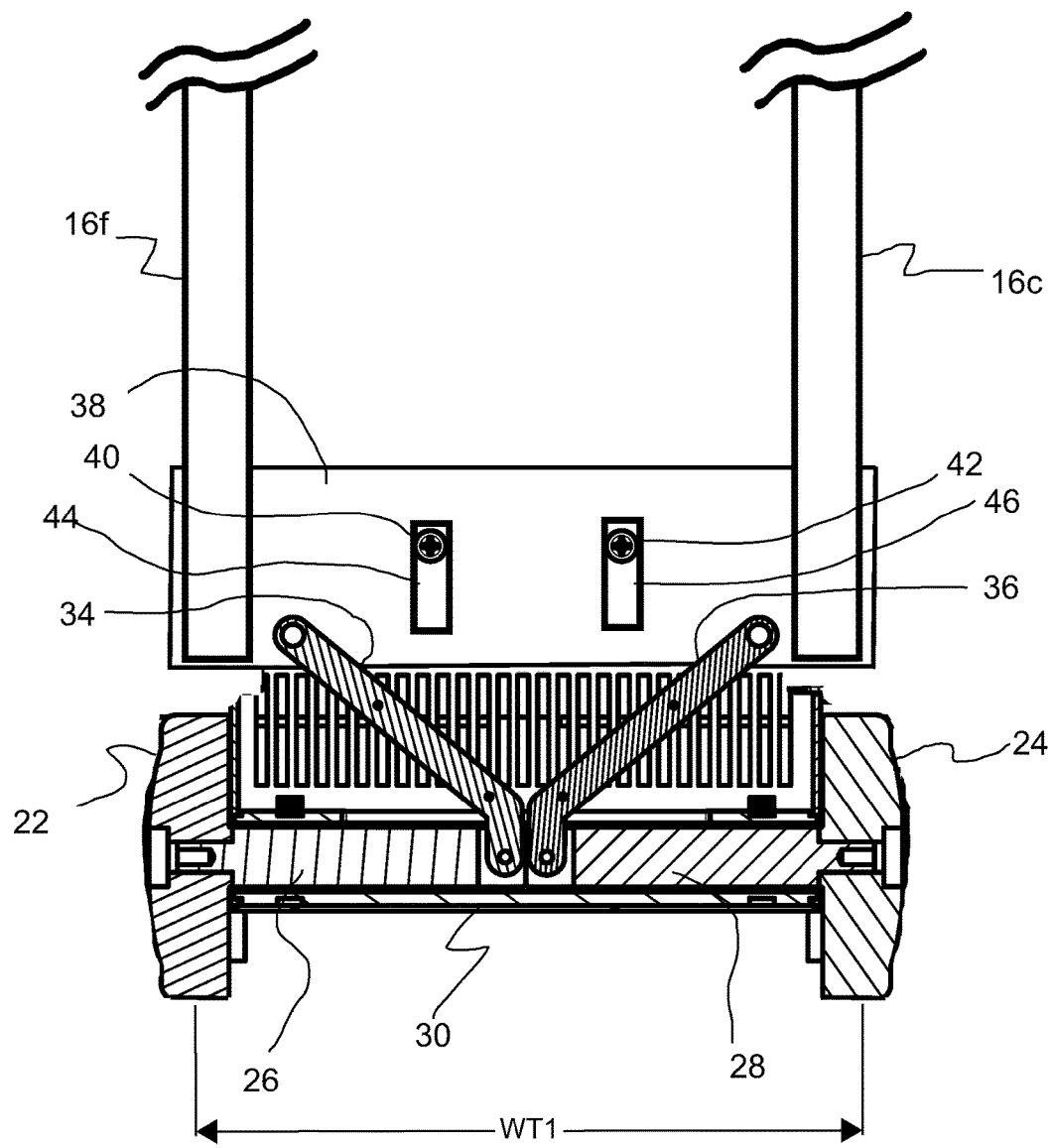
FIG. 18 is a magnified sectional partial view of FIG. 15 taken about border 182.

To facilitate transport, the pump unit 10 and carrier 12 have an axially extending wheel assembly 14 that can be extended remotely through the use of a handle or an actuator. FIGS. 12A-12B and 13A-13B further illustrate the pump unit 10 with a carrier 12 and an integral wheel assembly 14 capable of establishing a first and second stand-alone configuration. In FIGS. 12A, 15 and 18, wheels 22 and 24 are shown in the first stand-alone configuration retracted towards and flush with sidewall 122. When the wheel assembly 14 expands, wheel track and thus stability of the pump unit 10 during transport is increased from a first dimension WT1 shown in FIGS. 18 and 19 to a second dimension WT2 shown in FIG. 20. During tilted wheel transport, both wheels 22, 24 provide wheeled support for carrier 12 in the expanded or retracted positions.

Figure 13A:
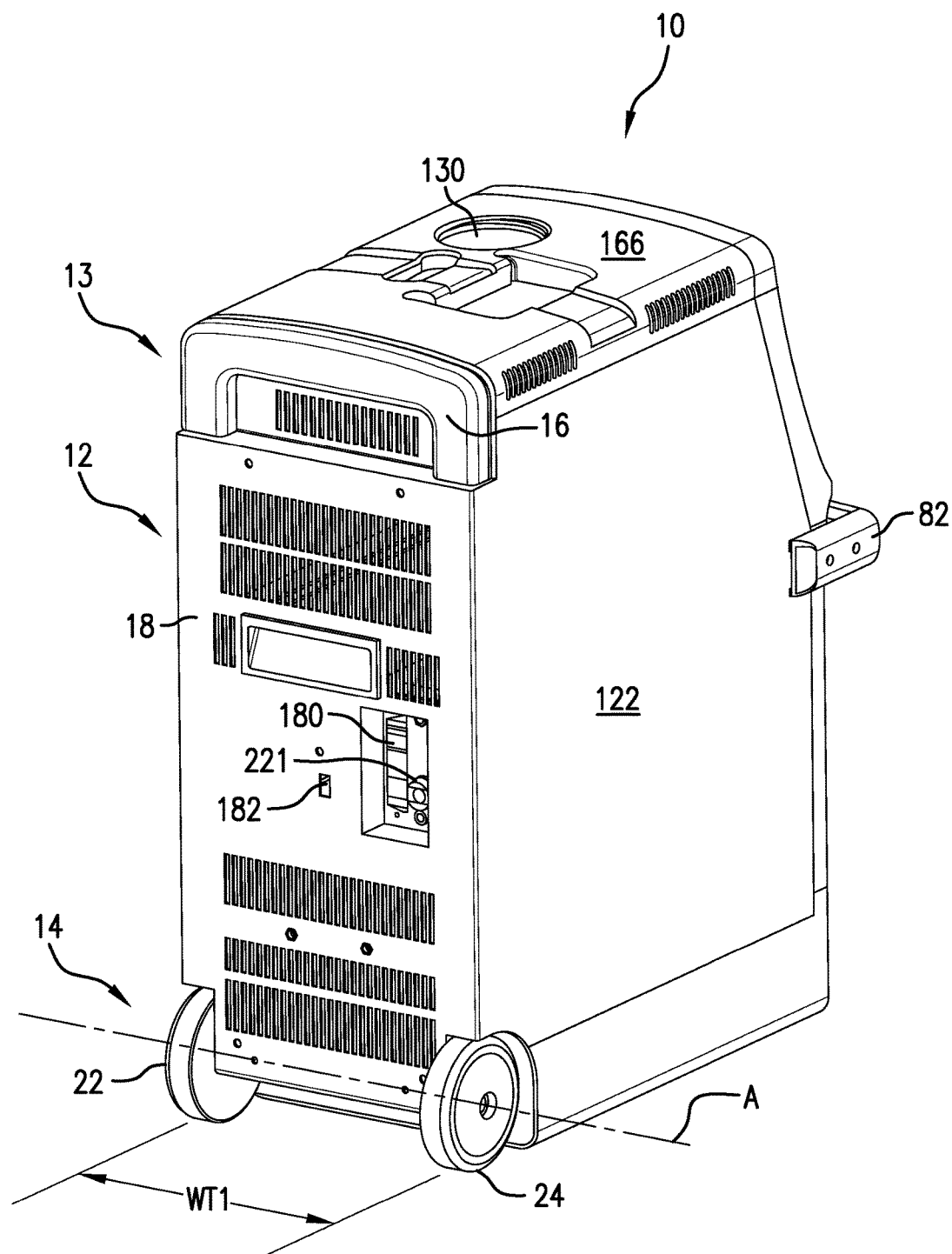
FIG. 13A is a rear perspective view of the pump unit of FIG. 12A.
Figure 14:
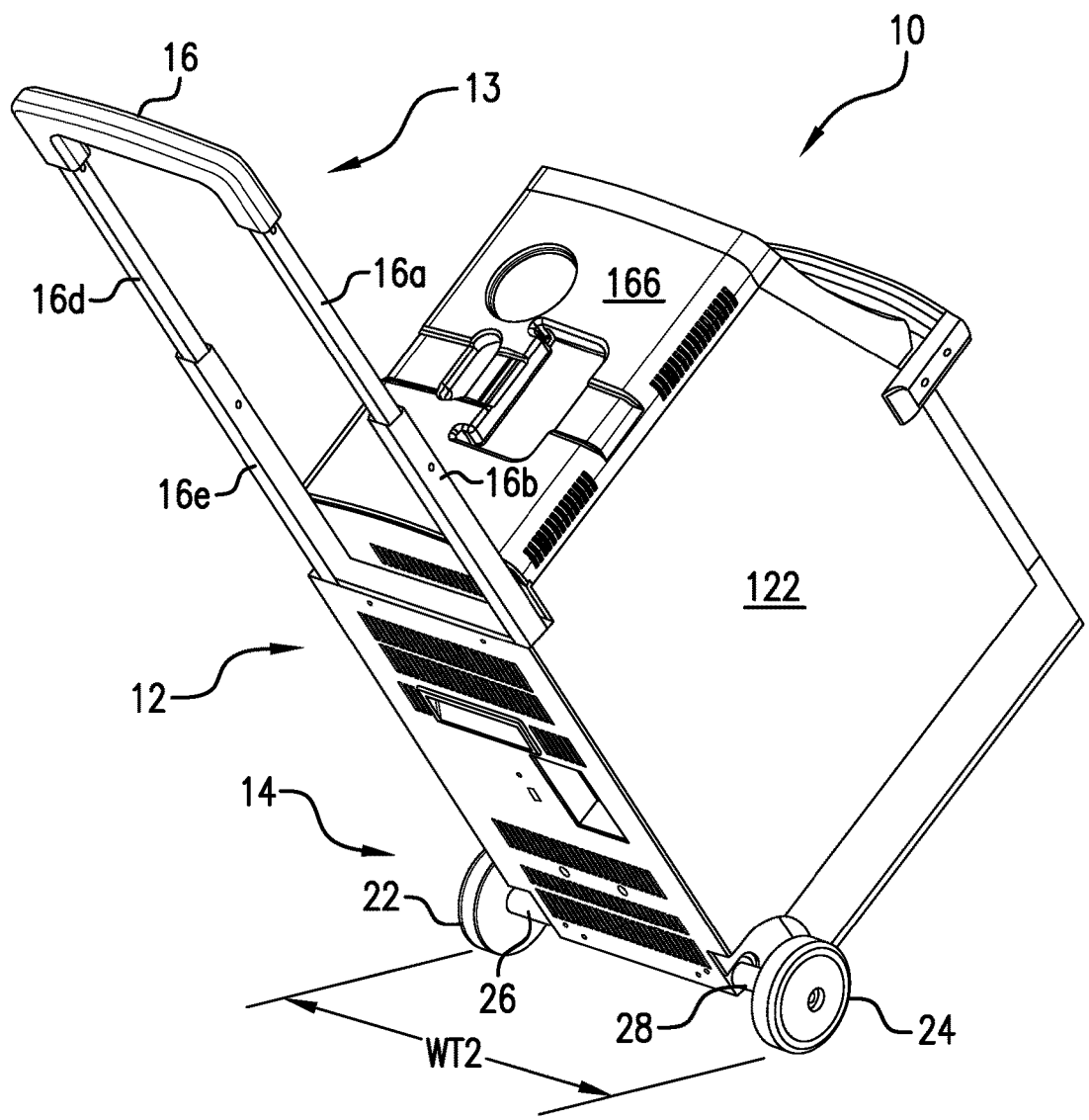
FIG. 14 is a perspective view of the pump unit of FIG. 11 with the monitor removed.

Similar to FIG. 11, FIG. 14 shows the pump unit 10 in a tilted position and in the expanded configuration (with monitor 64 not shown), consistent with how carrier 12 may be used during transport and in the stand-alone modular configuration. FIG. 14 further shows wheel assembly 14 in an expanded arrangement with a larger dimension wheel track WT2, larger than the first dimensioned wheel track WT1 shown in FIG. 13A.

Wheel assembly 14 can be extended or retracted remotely through the use of a handle or an actuator. For the purposes of this disclosure, "remote" may relate to locations beyond a local proximity, such as beyond the wheel area or local proximity of wheel assembly 14 as demarcated by reference border 199 in FIG. 11. The use of handle grip 16 of handle assembly 13 to expand the wheel track of wheels 22, 24 allows safe and uninterrupted portability of the pump unit 10 during tilted wheeled transport without requiring the user to pause, stoop down, or otherwise interrupt the delivery of patient care and monitoring.

Figure 12B:
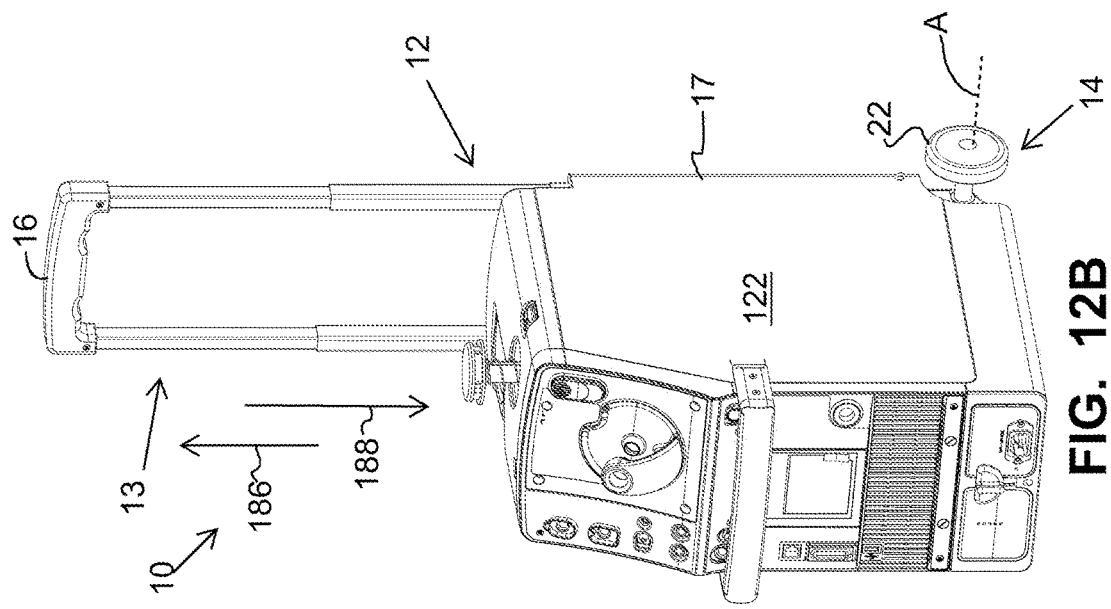
FIG. 12B is a perspective view of the pump unit of FIG. 12A with a monitor adapter protruding from atop surfaced, wheels expanded, and handle extended.
Figure 12A:
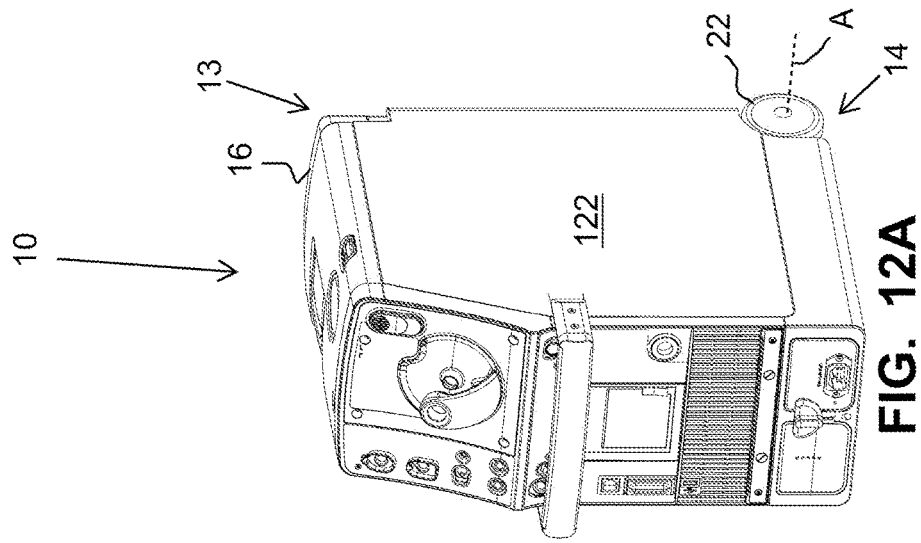
FIG. 12A is a perspective view of a pump unit according to an example embodiment of the present invention.
Figure 13B:
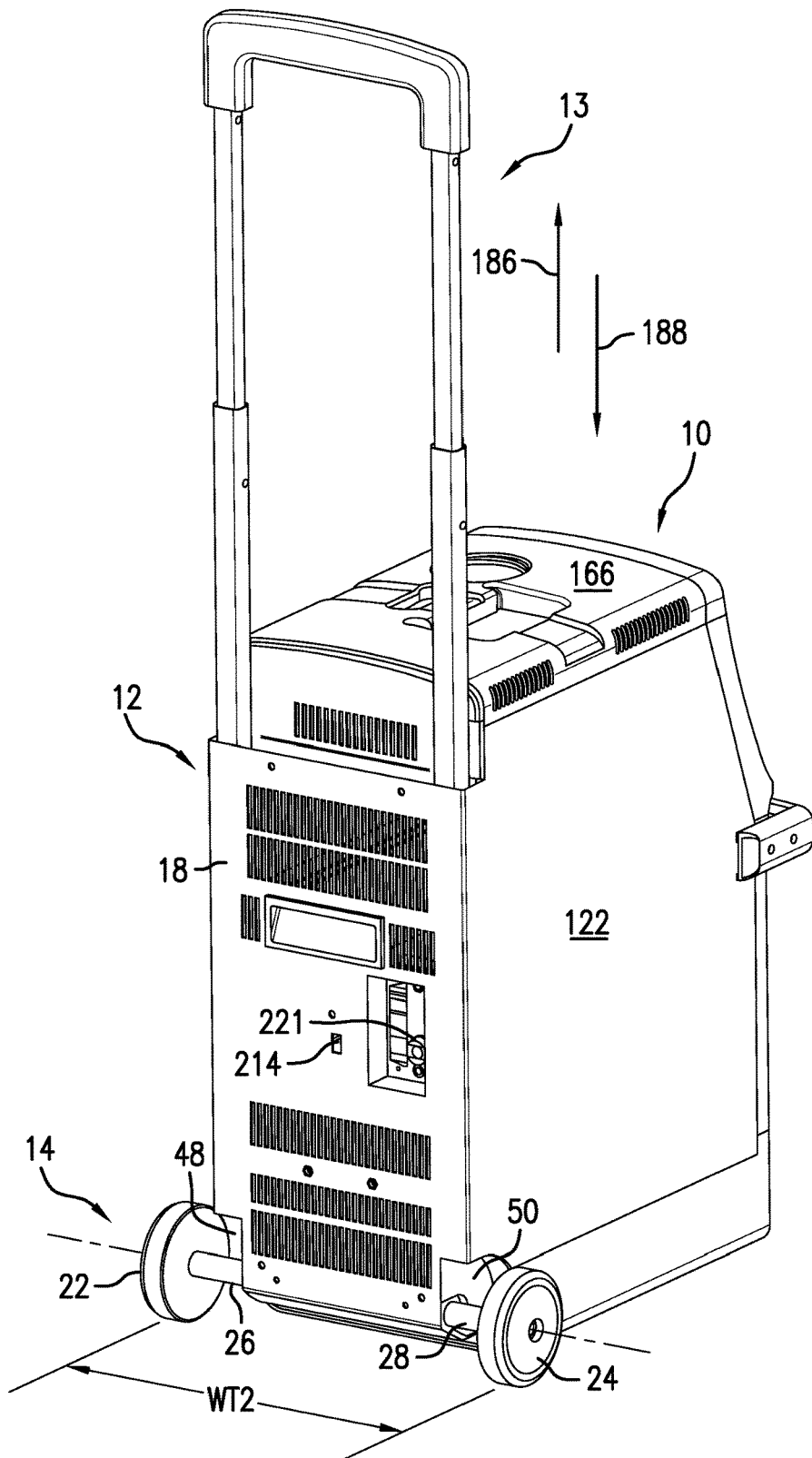
FIG. 13B is a rear perspective view of the pump unit of FIG. 12B.

In FIGS. 12A and 13A, handle grip 16 of retractable handle assembly 13 is shown to be retracted or otherwise moved to a first position, i.e., towards axis A in the direction 188. In a second stand-alone configuration shown in FIGS. 12B and 15B, wheels 22, 24 are extended away from each other and side wall 122 caused in part by movement of handle grip 16 remotely from wheel assembly 14 to a second position. Remote movement of handle grip 16 preferably involves the extension of the handle in a direction 186 away from axis A, although other embodiments and arrangements are possible.

As can be seen in FIGS. 12B and 15B, when the handle assembly 13 is extended to the second position (e.g., away from axis A), wheels 22, 24 of wheel assembly 14 are configured to extend or expand outwards from each other, preferably in an automatic arrangement, manually controlled remotely from the wheel locations. As an alternative to such manual control, motors or non-manual sources of energy may be used to control the wheel movement towards and away from each other.

The mechanisms for controlling the wheel assembly 14 with the handle assembly 13 will be explained in greater detail. FIGS. 15 and 16 show the carrier 12 attached to a rear portion of pump unit 10 in both extended and retracted positions, respectively. In FIG. 15, the wheel assembly 14 and handle assembly 13 are retracted and are nearly flush with side wall 122 (FIG. 139) and top surface 166 of pump unit 10, respectively. In FIG. 16, the wheel assembly 14 and handle assembly 13 are extended.

Figure 17:
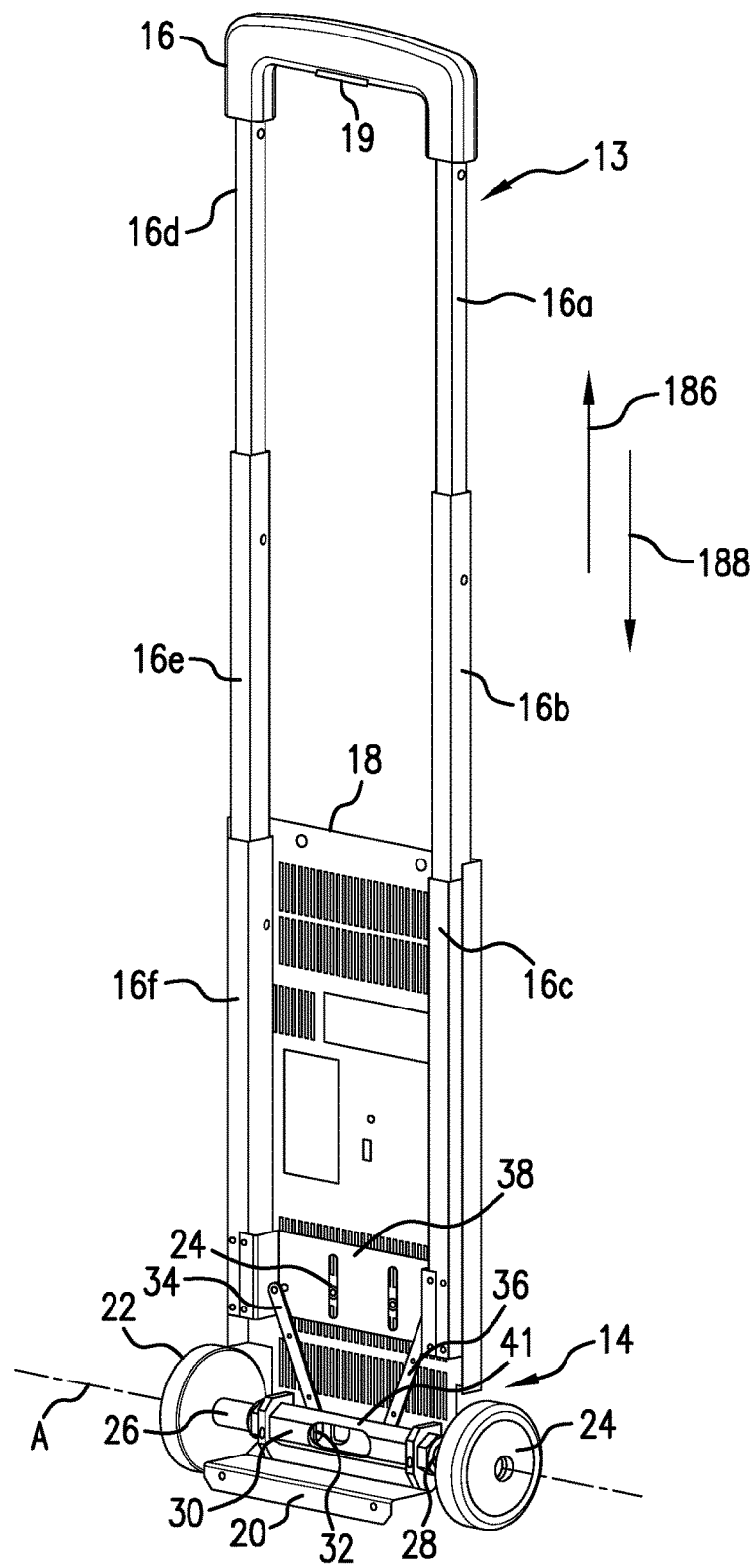
FIG. 17 is a perspective view of the carrier of FIG. 16.

FIG. 17 is a perspective view of the carrier 12 shown in FIG. 16. With the rest of pump unit 10 removed, the mechanism used to expand and retract the wheel assembly 14 is exposed. The handle assembly 13 of FIG. 17 includes a handle grip 16 and multiple generally parallel and telescoping tube-like posts 16*a*, 16*b*, 16*c*, 16*d*, 16*e*, and 16*f*. Alternatively, one telescoping tube-like post may be employed. More or less posts may be used depending on the desired length and intended compactness of the extended handle assembly 13. Also, although shown having a U-shape, the handle assembly 13 may have different shapes and configurations. For example, the handle assembly 13 may comprise a single line of one or more telescoping posts.

Referring to FIG. 17, posts 16*c* and 16*f* are connected to a back plate 18, which closes a back end of the pump unit 10 when connected to the pump unit connector plate 20. The handle assembly 13 may include a mechanism for reversibly locking handle grip 16 in the extended and/or retracted positions with respect to all or a portion of posts 16*a*-16*f*. Such mechanisms are well known in the art, including, for example, a depressible button 19. Depressible button 19 may control the engagement of posts 16*d* and/or 16*a* to one or more of posts 16*b*, 16*c*, 16*e*, and 16*f*, and thus the handle 16 can be used to selectively engage and disengage the locking mechanism. Button 19 thereby allows for handle 16 to be positioned with respect to one or more positions to all or a portion of posts 16*a*-16*f*. Posts 16*a*-16*f* may also include spring biased buttons or detents on their ends which interlock the posts in the extended position until the buttons are depressed and/or the posts are forced back into each.

Wheel assembly 14 includes two wheels 22, 24 mounted on half axles 26, 28. The half axles 26, 28 rotate about their longitudinal axis, and optionally may share a common axis A within retainer (or guide) 30 as the pump unit 10 is wheeled about. The half axles 26, 28 slide along axis A within retainer 30 as the wheel assembly 14 is expanded and retracted thereby adjusting the wheel track. Preferably, the half axles do not rotate, but the wheels 22, 24 are configured to rotate with respect to axles 26, 28. A cut-out 32 in retainer 30 exposes the innermost end of each half axle 26, 28.

Half axle 26 is pivotally connected to linkage 34 and half axle 28 is pivotally connected to linkage 36, both of which are pivotally connected to a guide plate 38. Guide plate 38 is fixedly connected to posts 16c and 16f. Guide plate 38 is slidingly connected to back plate 18 via guides 40, 42 which slide in slots 44, 46 of guide plate 38. Linkages 34, 36 connect to innermost portions of half axles 26, 28 and extend through an elongate opening 41 on the top of retainer 30.

When handle grip 16 of handle assembly 13 is fully retracted, or directly or indirectly interlocked with posts 16c and 16f and compressed towards axis A along direction 188, half axles 26, 28 are forced towards each other moving wheels 22, 24 laterally towards sidewall 122, preferably fully or partially into recesses 48, 50. Similarly, when handle grip 16 of handle assembly 13 is extended, or directly or indirectly interlocked with posts 16c and 16f and extended away from axis A along direction 186, half axles 26, 28 are forced away from each other moving wheels 22, 24 laterally outwards of recesses 48, 50 and away from sidewall 122 on both sides of the pump unit 10. This provides for expansion of the footprint and wheel track for increased stability of the pump unit 10 during tilted wheeled transport.

FIG. 18 is a supplemental view illustrating a partial cross section of carrier 12 taken about border 182 of FIG. 17, sectioned through axis A. As shown in FIG. 18, half-axles 26, 28 are preferably solid in cross section to provide for strength and resistance to bending when cantilevered beyond the left and right contacting surface of retainer 30.

Figure 19:
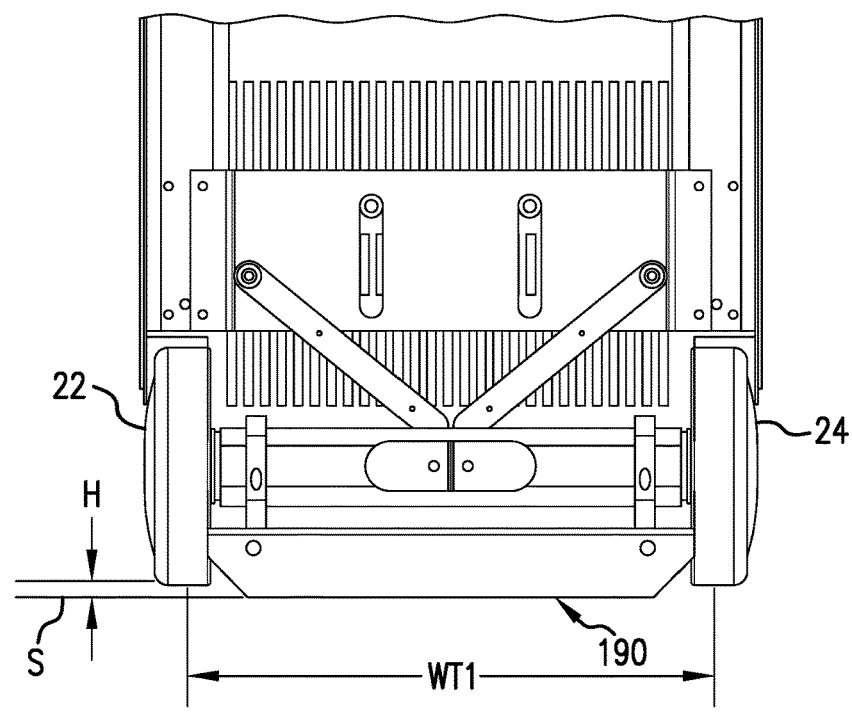
FIG. 19 is a magnified partial view of FIG. 15 taken about border 182.
Figure 20:
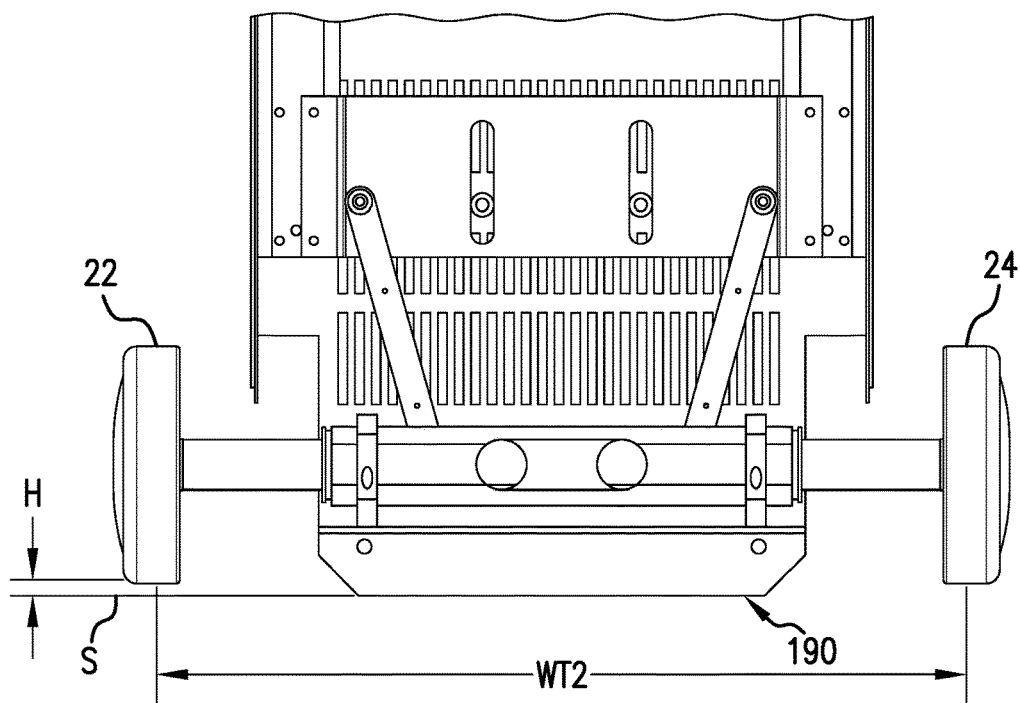
FIG. 20 is a magnified partial view of FIG. 16 taken about border 184.

FIGS. 19 and 20 illustrate partial views of FIGS. 15 and 16 taken about borders 182 and 184 respectively. Both FIGS. 19 and 20 show a bottom surface 190 of pump unit 10, or carrier 12. In the embodiments shown in FIGS. 19 and 20, when the bottom surface 190 rests on the flat surface S, the pump unit 10 and/or carrier 12 is allowed to rest with a clearance H established beneath the bottom of wheels 22, 24. This static clearance provides for a operator to remotely adjust wheels 22, 24 of wheel assembly 14 from a first wheel track dimension WT1 to a second wheel track dimension WT2 in an unencumbered manner (i.e., absent friction caused by surface S). Additionally, the bottom surface 190 is shown to be beneath the bottom of wheels 22,24, and therefore also at a lower elevation than the axis A of wheels 22,24. Furthermore, wheels 22 and 24 remain parallel to their first retracted configuration when moved to their second expanded configuration. Alternatively, only one of wheels 22 and 24 may be configured to move from the first to the second position, and still achieve the improved and expanded wheel track as illustrated herein.

Figure 21:
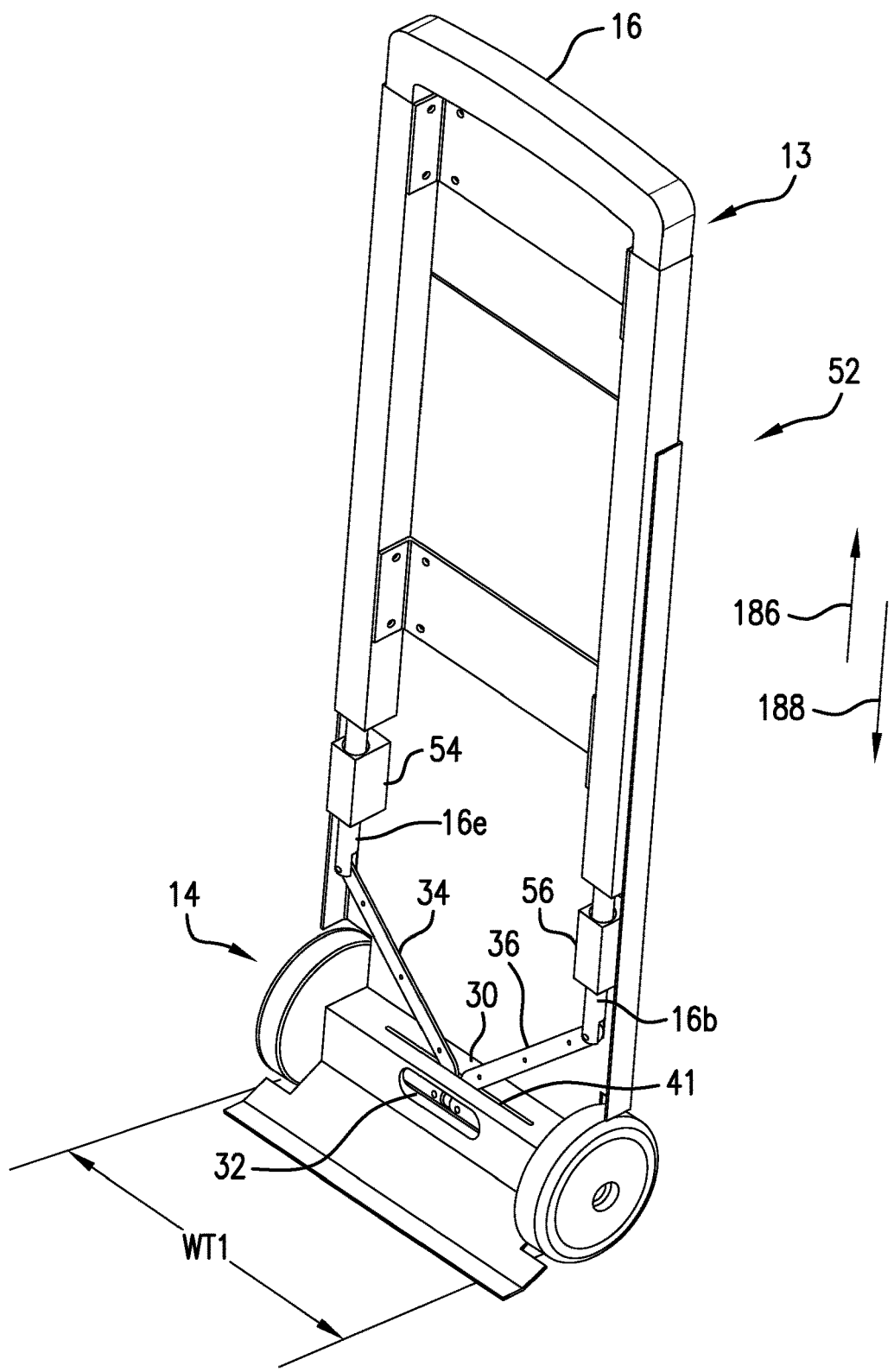
FIG. 21 is perspective view of a carrier according to an example embodiment of the present invention with the handle and wheel assemblies retracted.
Figure 22:
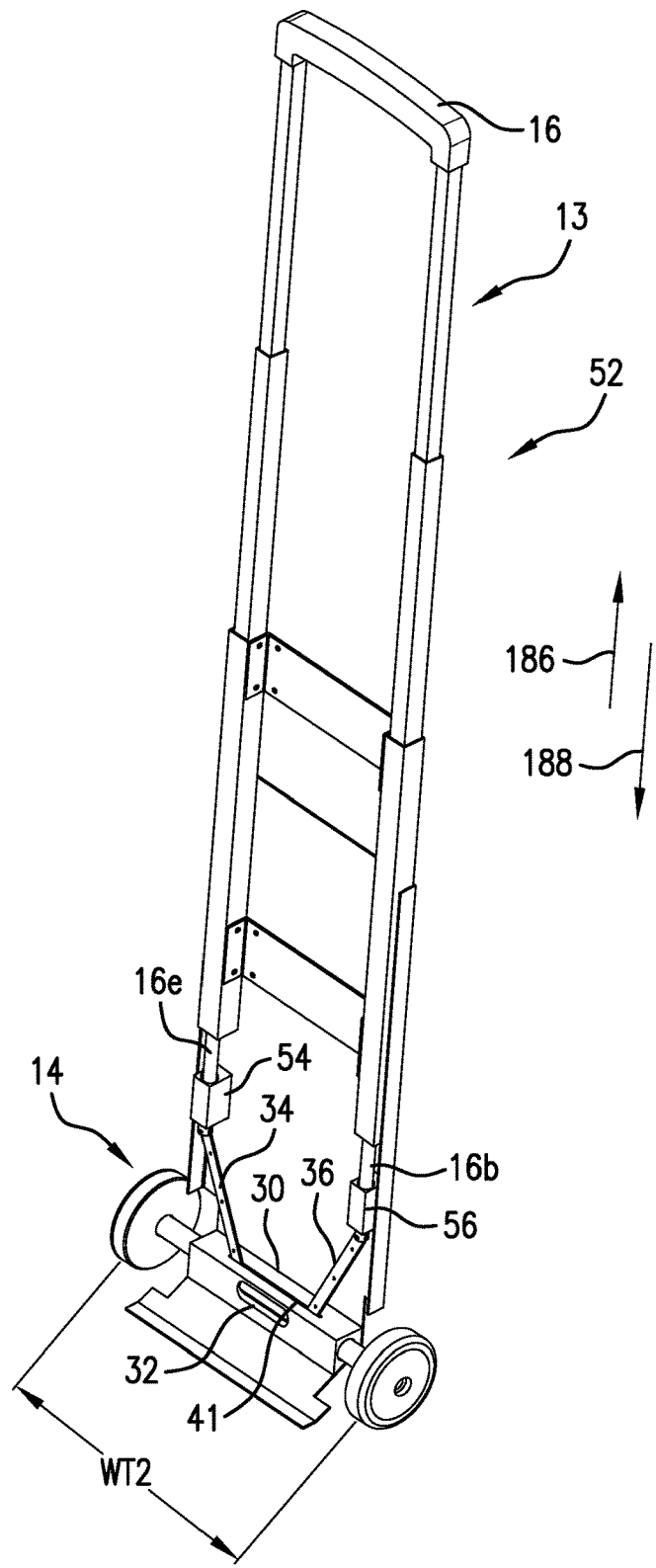
FIG. 22 is a perspective view of the carrier of FIG. 21 with the handle and wheel assemblies extended.

FIG. 21 illustrates an alternative carrier 52 consistent with embodiments of the present disclosure. The alternative carrier may be used with all embodiments of the pump unit 10 and cart 9, as demonstrated in the Figures. Unlike carrier 12 illustrated for example in FIGS. 14 through 17, which uses linkages directly connected to a guide plate, carrier 52 uses linkages 34, 36 connected directly to post 16b and 16e, whose lower ends have a tube-like shape. FIG. 22 shows the carrier 52 with the handle assembly 13 and wheel assembly 14 extended. With the handle assembly 13 fully extended, linkages 34, 36 butt up against stops 54, 56.

In an alternative embodiment capable of being utilized with either carrier 12 or carrier 52, the wheels 22, 24 may be decoupled from the handle assembly 13. In other words, extending and retracting the handle assembly 13 will not cause the wheels 22, 24 move in and out of recesses 48, 50. Rather, a servo or motor (e.g., placed between the half axles 26, 28) may be used to laterally shift half axles 26, 28 back and forth along axis A. The servo or motor may be manually triggered or remotely triggered. For example, a button or switch located anywhere on the pump unit 10, including handles connected thereto, may be used to manually trigger the servo or motor. Alternatively, extension of the handle assembly 13 may trigger the switch and cause the motor or servo to shift the wheels 22, 24 apart. In an alternative embodiment, a remote control may be used to trigger the servo or motor. Optionally, an automated switch configured to detect a parameter of the cart 9 (such as when the carrier is in proximity to the cart) can perform the triggering.

In yet another embodiment, the pump unit 10 tray have one or more sensors capable of interpreting a vertical orientation of the pump unit 10, as well as whether or not the pump unit 10 is inside cavity 11 of cart 9. The sensor may be triggered when the pump unit 10 is tilted (as in FIGS. 13 and 16) to an acute angle 103, preferably in a range of less than eighty-five degrees, more preferably less than seventy-five degrees. Upon triggering of the sensor, a controller will activate the motor or servo to expand the wheel assembly. This can occur during to or prior to actual movement of pump unit 10 in the stand-alone configuration.

A feature that further modularizes medical system 4 is the utilization of a dedicated reservoir or tank to supply a shuttle gas to a patient side of a pneumatic isolator. In use, the intra-aortic balloon pump inflates and deflates an intra-aortic balloon through the use of the pneumatic isolator and compressor. Helium is the gas of choice for the patient side due to its low density and viscosity. Gradual helium loss occurs when the balloon pump is used continuously and requires replenishing on an as-needed basis. In an example embodiment of the present invention, pump unit 10 may be configured to have its own dedicated helium reservoir or tank 286, as shown through cutaway 232 in FIG. 24 that functions as a first pressurized gas source for supplying gas to the patient side 326 of the pneumatic isolator 320. The dedicated tank may be sized smaller than typical tanks currently utilized in intra-aortic balloon pumps for periodic exchange or replacement. Additionally, the dedicated tank may be simplified to be directly connected to a fill manifold, thereby reducing components that would otherwise add mass to the intra-aortic balloon pump, potentially rendering a pump unit less suitable for ambulatory helicopter transport than otherwise desirable. Further in one embodiment, the dedicated tank may be a permanently integrated component of the pump unit 10 wherein the dedicated tank is irremovable or removable with difficulty so as to require partial or complete disassembly of the pump unit 10.

Figure 25:
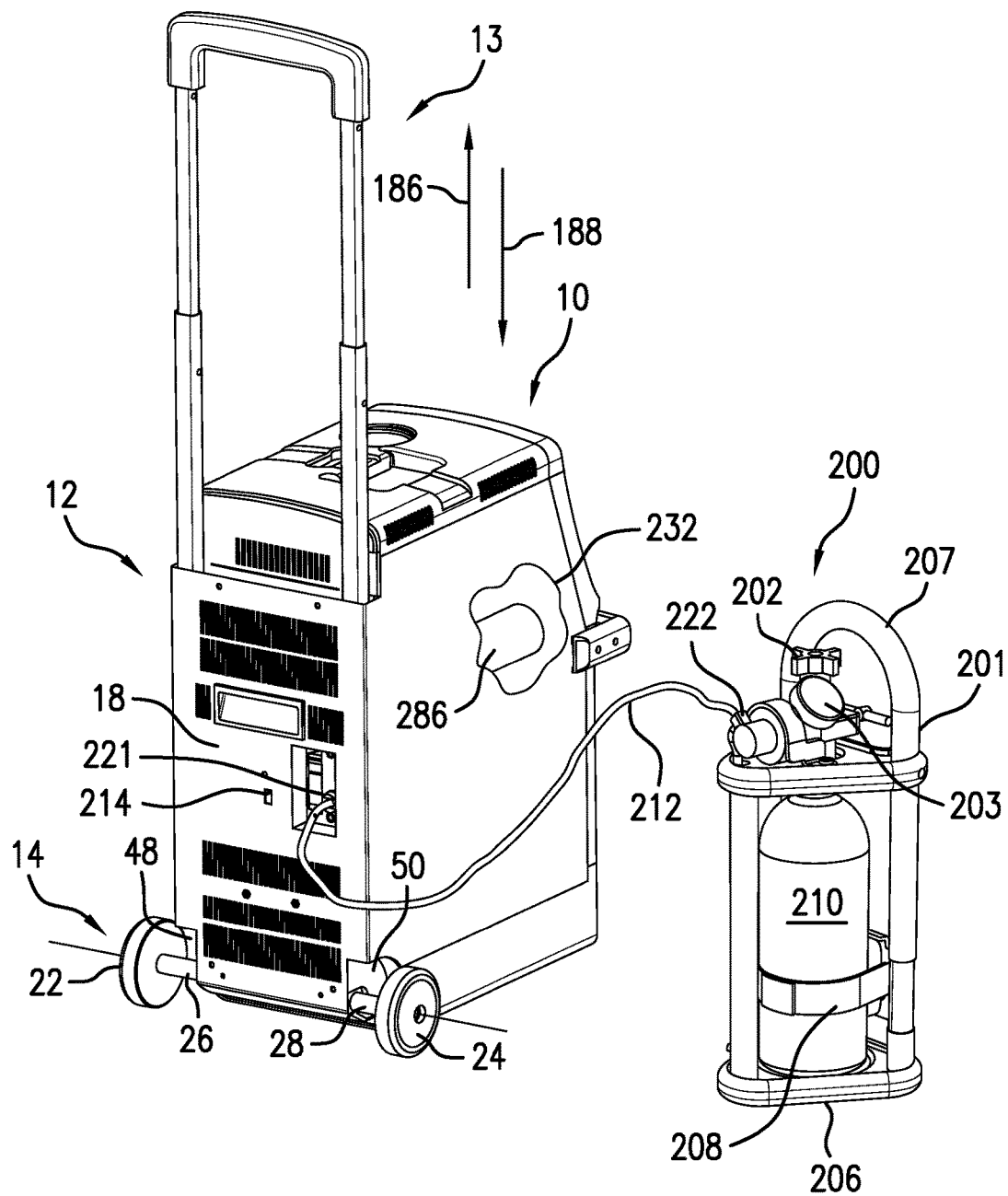
FIG. 25 is a perspective view of an example embodiment of a medical pump system according to the present invention.

To be usable both inside and outside a hospital setting, a fill system 338 within the pump unit 10 may be relatively small to accommodate short-term ambulatory helicopter use as well as longer-term hospital use. In an exemplary arrangement, in addition to a dedicated tank 286 that provides a sufficient amount of helium for limited short-term use (e.g., three days of normal balloon pumping therapy), the fill system 338 may further include one or more recharge tanks that functions as a second pressurized gas source which can be removably coupled to the dedicated tank 286 to replenish dedicated tank 286 as needed. In one embodiment, the recharge tank may be supported on the wheeled cart or a portable tank holder, as illustrated in FIGS. 24-25.

In an example embodiment, refilling of the dedicated tank 286 may be carried out with the assistance of a recharge tank located remote from the pump unit 10. Preferably, the recharge tank may optionally have an integral valve and be sized larger than the dedicated tank 286 used in the pump unit, e.g., sized larger than about a half liter of internal volume. In one embodiment, the recharge tank may have a volume of about 0.5 to about 1.5 liters. Exemplary recharge tanks include part numbers 0075-00-0024-03, 0075-00-0034-03, 0075-02-0001-03, 0075-02-0002-03, and 0202-00-0104 offered by Maquet Cardiovascular LLC, Wayne, N.J., 07470.

FIG. 24 shows by example a cart based recharge tank 288 (seen through cutaway 230). The recharge tank 288 may be stored internal to the cart, or attachable to an external portion thereof. In one embodiment, the recharge tank is located at or near the base of cart 9 (as shown in cutaway 230 of FIG. 24) and supported on a slidable surface of cart 9, such as a slidable tray (not shown), in a first position, the tray is stowed within an internal cavity the cart 9, as shown in FIG. 24. When the tray is extended to a second position protruding out from an exterior surface of the cart 9, a user is able to manipulate or replace recharge tank 288 as necessary. The tank 288 may also be readily and reversible connectable to pneumatic tubing or fittings within the cart 9 through a connector integral to the recharge tank 288.

In an alternative embodiment, the recharge tank 288 may be separate from the pump unit 10 or cart 9. For example, as shown in FIG. 25, a stand-alone tank holder 200 is enclosed in a frame 201 resting on a base 206, both of which serve to protect tank a recharge tank 210 from damage. Preferably a handle 207 is integral to the frame 201 to facilitate manual transport of the tank holder 200. The tank holder 200 also includes a strap 208 to further secure the tank 210 inside the holder 200.

The recharge tanks are useful for readily connecting to the pump unit 10 with ease, quickness, and minimal user intervention. More specifically, helium in tank 286 may be replenished using helium in tank 288 when the pump unit 10 is docked to cart 9. Alternatively, the helium in tank 286 may be replenished using helium in the stand-alone portable tank 210 when the pump unit 10 is taken out of cart 9.

For example, as shown in FIG. 25 stand-alone tank 210 has near the top region of the tank holder 200 a tubing connector 222, a valve 202 and regulator 203. Tubing 212 extends from the tubing connector 222 and is configured to connect tank 210 to dedicated tank 286 of the pump unit 10 through a pneumatic interface 221 on the pump unit 10. After the dedicated tank 286 is sufficiently re-charged with helium, the tubing 222 may be disconnected from the pump unit 10 and the pump unit 10 can be safely used for a period of time before requiring an additional helium recharge.

Alternatively, the stand-alone portable tank 210 or recharge tank 288 may also be connectable to the pump unit 10 through a carefully constructed pneumatic interface on both the cart 9 and the pump unit 10. Pneumatic fittings on pump unit 10 and cart 9 can be configured to reversibly engage one another and establish fluid communication when the pump unit 10 is docked to the cart 9. Preferably, the pump unit 10 should be fully docked in the cart's cavity 11 when fluid communication is established. When docked, a pneumatic fitting 220 internal to the cart 9 engages the helium interface connector 221 on the back side of pump unit 10 to provide a pneumatic connection and allow for recharging of tank 286.

Figure 26:
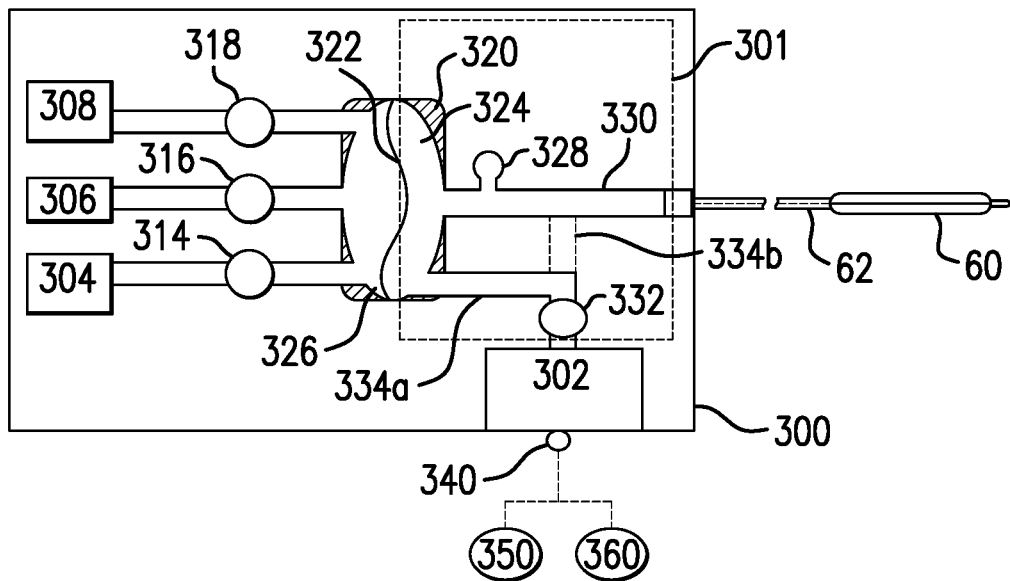
FIG. 26 is a schematic diagram of an IABP pneumatic system of an embodiment of a medical system.

Example balloon pump pneumatics are shown in U.S. Pat. No. 8,133,184, herein incorporated by reference in its entirely. A variation of the pneumatics useful for carrying out the recharging of the internal tank 286 is described herein. FIG. 26 shows a schematic representation of a pneumatic system 300 for intra-aortic balloon pump 10 when connected to an intra-aortic balloon 60 and balloon catheter 62 through a fill/purge line 330. The IABP pneumatic system 300 comprises a pneumatic isolator 320 having a membrane 322 for isolating a patient side 324 from a drive side 326. A drive side pressurized gas source 304 and vacuum source 306 are fluidically connectable to the drive side 326 through pressure source valve system 314 and vacuum source valve system 316, respectively. Pressure within the drive side pressurized gas source 304 and vacuum source 306 is controlled by a plurality of valves (not shown) and one or more compressors 290 (see FIG. 24). Optionally, a vent 308 may be fluidically connectable to the drive side 326 of membrane 322 along with a vent valve system 318 positioned between the vent 308 and the pneumatic isolator 320.

A pneumatic manifold 301 is designed to encompass and manage the delivery of helium to and from the balloon 60. The pneumatic manifold 301 comprises a shuttle gas transducer 328 as well as an isolator valve 332 for controllably isolating a fill manifold 302 from the pneumatic manifold 301. Optionally, the pneumatic manifold 301 may have a dryer (not shown) for removing water vapour from the gases used on the patient side of the membrane after hours of continuous use. The fill manifold 302 may be fluidically coupled to the pneumatic manifold 301 directly (see path 334b) or indirectly through the patient side 324 of isolator 320 (see path 334a). Valve 332 functions to isolate the pneumatic manifold 301 IABP circuit with helium from the fill manifold 302.

Figure 27:
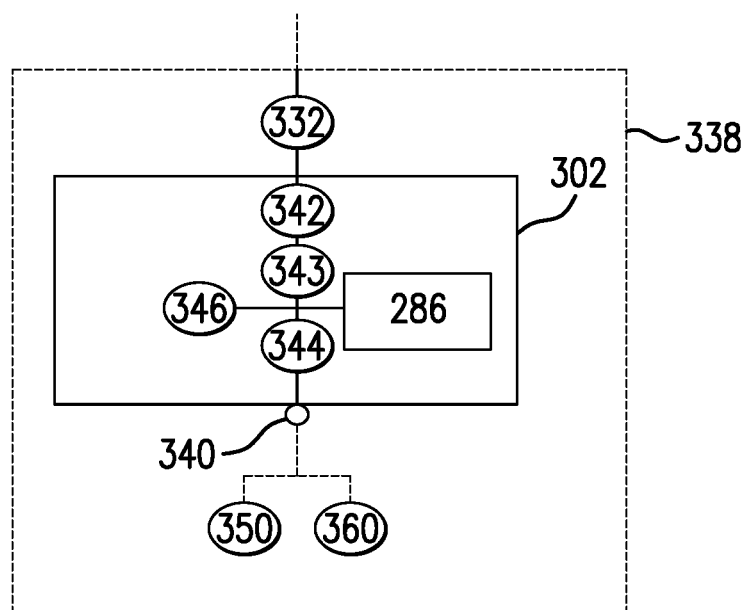
FIG. 27 is an additional schematic diagram of a fill manifold of FIG. 26.

In FIG. 27, which shows a fill system 338, includes a fill manifold 302 has a reservoir or tank 286 (e.g., a helium reservoir), a first valve arrangement 342, and a second valve arrangement 344. The first valve arrangement 342 may include one or more valves located in parallel or series. The second valve arrangement 344 may comprise a single one-way valve enabling gas flow towards tank 286. The recharge tank 228 can be fluidically coupled to the first valve arrangement 342 by the valve coupling 340 e.g., previously described as helium interface connector 221. A pressure transducer 346 may be employed to ascertain the pressure in the tank 286 to help monitor when the tank is in need of refilling. The volume of tank 286 may be chosen based on the amount of time the pump unit will be used without requiring a refill. The volume may range, for example, from about 50 cubic centimeters to about 400 cubic centimeters. A more preferable range is about 100 to about 200 cubic centimeters. A most preferred volume is about 150 cubic centimeters.

A pressure regulator 343 is located between reservoir tank 286 and the first valve arrangement 342 to limit the pressure available to the pneumatic manifold 301. The second valve arrangement 344 allows for recharging the fill volume and pressure of gases in the reservoir tank 286 when connected to a recharge tank. One or more connectors or fittings 340 may be utilized in order to connect the IABP pneumatic system 300 to one or more previously described recharge configurations. As shown in FIGS. 26 and 27, the cart-based recharge tank and stand-alone recharge tank configurations are represented as 350 and 360 respectively.

Another feature that further modularizes medical system 4 is the utilization of dual power supplies. As with the dual helium tanks, medical system 4 may be used with our without this feature. Dual power supplies enable the medical system 4 to be operated as a cart-based system or as a standalone system. Cart 9 has a power supply 240 that can be used to power medical system 4 when the pump unit 10 is integrated with cart 9. Power supply 240 draws current through an external power supply (e.g., an A/C power supply, wall outlet), and may convert the voltage from 110 V A/C or 220 V A/C to a fixed DC voltage (e.g., 15V DC)

and provides power to the components of pump unit 10 and monitor 64. When pump unit 10 is removed, it can be operated as a standalone system using one or both of power supplies 248 and 246. Power supply 248 can be a battery, e.g., a DC lithium-ion battery, or optionally may be an AC to DC converter capable of outputting DC current from an external AC power source. Battery-based sources of power facilitate transportability of pump unit 10 while externally sources of power provide convenience when the pump unit 10 is near a power outlet. The dual power supply system is described in detail in U.S. patent application Ser. No. 13/089,128 entitled "Multi Power Source Power Supply," which is wholly incorporated by reference herein.

In an exemplary embodiment, modularity is further enhanced by shifting data processing, e.g., graphics generation, from one or more processors in the pump unit 10 to one or more processors in monitor 64. In prior art IABPs, the video capability was a 640×480 monochrome out. Outputting such video graphics through a long wire was feasible. However, in an exemplary embodiment, monitor 64 outputs 1024×768 full color video graphics and aliases at 18 bits per pixel. To output such data over wire 70 of the length existing between the pump unit 10 and cart 9 when separated or integrated, the wire would need to be prohibitively thick, add weight, and not provide for the bendability needed to frequently transfer the pump unit 10 from a stand-alone configuration to a cart-based configuration. To overcome such issues, a first CPU 252 is included in the pump unit 10 to collect data and communicate with a separate second CPU 250 in the monitor 64 through wire 70. Wire 70 is a cord, e.g., coiled, including four pairs of power cables and 2 pairs of Ethernet cables. The CPU 250 in monitor 64 then outputs display lists to a graphics chip 254 in the monitor 64, which processes and translates data into viewable graphics displayable on the monitor 64.

For example, patient data measured using an intra-aortic balloon catheter 60 (see FIG. 1) is collected by the first CPU in the pump unit 10 and then transferred to the second CPU 250 in the monitor 64 via wire 70. This transferred data is then processed by the second CPU 250 for display of relevant patient information on the patient monitor 64, such as an ECG wave or pressure wave. An example CPU is the Motorola PowerPC CPU, which can be used in both pump unit 10 and monitor 64. An example graphics chip is an AMD brand ATI M54 chip. Alternatively, an FPGA (field programmable gate array) can be used as a single chip solution in monitor 64. Additionally, the second CPU 250 is used to process user input data and to execute the pump display interface 68, e.g., touch screen interface.

Those skilled in the art can appreciate from the foregoing description that the present invention can be implemented in a variety of forms and is not limited to intra-aortic balloon pumps. The carrier of the present invention can be used and/or connected to other devices requiring stable transport. Further, the inventive modularity aspects of the present invention can be applied to other devices, e.g., medical devices, that would benefit from multiple configurations suited for different operating conditions and environments. Therefore, while the embodiments of this invention have been described in connection with particular examples thereof, the true scope of the embodiments of the invention should not be so limited since other modifications and variations will become apparent to the skilled practitioner upon a study of the drawings and specification. Such modifications and variations are considered to be within the purview and scope of the appended claims and their equivalents.

The invention claimed is:

1. An intra-aortic balloon pump configured for tilted wheel transport, comprising:
a frame, a pump comprising a pump body, the pump disposed within the frame, a display device associated with the pump, a control unit configured to control the pump, a handle assembly connected to the frame and comprising a handle grip, and a wheel assembly connected to the frame, wherein the wheel assembly comprises a first and second wheel, each movable linearly between (i) a retracted position defining a first wheel track in which the wheels are spaced apart a predetermined distance and orientation, and (ii) an extended position defining a second wheel track larger than the first wheel track in which the wheels are spaced apart a distance greater than the predetermined distance yet have essentially the same predetermined orientation;
wherein linear movement of the wheels from the retracted position to the extended position is manually controlled by linear movement of at least a portion of the handle assembly from a first position to a second position, the second position spaced apart from the first position and wherein the first and second wheels are located towards a vertical side of the pump body and to accommodate tilted wheel support to the pump body along a horizontal and flat surface when the pump body is maintained in a tilted orientation with respect to the horizontal and flat surface and gripped at the handle grip by a user.

2. The intra-aortic balloon pump according to claim 1, wherein the handle assembly includes a plurality of telescoping members.

3. The intra-aortic balloon pump according to claim 1, wherein each of the first wheel and second wheel is connected to a separate axle.

4. The intra-aortic balloon pump according to claim 1, wherein the frame has a bottom surface for resting on a ground surface, and an axis of one or both of the first and second wheel is located at an elevation higher than the frame's bottom surface.

5. The intra-aortic balloon pump according to claim 4, wherein the bottom of each of the first and second wheel is located at an elevation higher than the bottom surface of the frame yet lower than the elevation of the axis of one or both of the first and second wheel.

6. The intra-aortic balloon pump according to claim 1, wherein the first and second wheels are the only wheels used for providing wheeled support to the body in both the extended and retracted positions when the body is maintained in the tilted orientation with respect to the horizontal and flat surface and gripped at the handle grip by the user.

7. A method for enhancing the stability of an intra-aortic balloon pump during transport, the intra-aortic balloon pump comprising a frame, a pump disposed within the frame, a control unit configured to control the pump, a handle assembly connected to the frame, and a wheel assembly connected to the frame and to the handle assembly, the wheel assembly provides for an adjustable wheel track and comprises a first wheel and a second wheel, each movable linearly, the method comprising the step of:
moving the first wheel and the second wheel from (i) a retracted position defining a first wheel track in which the wheels are spaced apart a predetermined distance, to (ii) an extended position defining a second wheel track larger than the first in which the wheels are spaced apart a distance greater than the predetermined distance, wherein linear movement of the wheels from the retracted position to the extended position is manually controlled by linear movement of the handle assembly.

8. The method according to claim 7, further comprising the step of moving at least a portion of the handle assembly from a first position to a second position spaced apart from the first position so as to trigger the movement of the wheels from the retracted position to the extended position.

9. A modular portable intra-aortic balloon pump, comprising:
(a) a wheeled cart with at least one caster for rolling on a ground surface, and
(b) a pump unit,
the pump unit comprising a frame, a pump disposed within the frame, a display device in electronic communication with the pump unit, a control unit configured to control the pump, a wheel assembly connected to the frame, wherein the wheel assembly comprises a first and second wheel, each manually movable between (i) a retracted position defining a first wheel track in which the wheels are spaced apart a predetermined distance and (ii) an extended position defining a second wheel track larger than the first wheel track in which the wheels are spaced apart a distance greater than the predetermined distance, wherein the first and second wheels are configured to provide wheeled support to the pump unit along a horizontal and flat ground surface in both the extended and retracted positions when the pump unit is in a tilted orientation with respect to the horizontal and flat ground surface, wherein the first wheel and the second wheel in the first position sharing a common axis with the first wheel and the second wheel in the second position, the common axis having an orientation that is fixed with respect to the frame and the axels of the first and second wheels extend from the wheels to the frame and are connected to the frame,
wherein the wheeled cart is configured with a cavity to removably and securely house and transport the pump unit and the wheel assembly such that the pump unit is elevated at a fixed height with respect to the ground surface when at least partially enclosed by the cavity, wherein the wheeled cart is further configured to transport the pump unit using the at least one caster but without use of the first and second wheels, and wherein the pump unit is also transportable independently in the tilted orientation via the first and second wheels when removed from the cavity of the wheeled cart.

10. The modular portable intra-aortic balloon pump according to claim 9, wherein the cavity of the cart has a cavity entrance and one or more sidewalls, and the pump unit is configured to be removably received into the cavity through the cavity entrance such that the pump unit while received within the cavity either (i) makes contact with at least one of the one or more sidewalls of the cavity, (ii) is adjacent to at least one of the one or more sidewalls of the cavity, or (iii) makes contact with and is adjacent to at least one of the one of the one or more sidewalls of the cavity.

11. The modular portable intra-aortic balloon pump according to claim 10, wherein the pump unit cannot fit through the cavity entrance when the first and second wheels are each in the extended position.

12. The modular portable intra-aortic balloon pump according to claim 10, wherein the cavity entrance is configured to allow at least partial insertion and removal of the pump unit horizontally into and out of the cavity, and wherein a release mechanism having a release actuator on at least one of the cart or pump unit is configured to establish releasable securement of the pump unit with respect to the cavity.

13. The modular portable intra-aortic balloon pump of claim 9, further comprising a handle assembly connected to the pump unit and configured to telescopically move between a first handle position and a second handle position, wherein movement of the handle assembly from the first position towards the second position causes relative movement of the first wheel towards and second wheel.

14. An intra-aortic balloon pump (IABP) system, comprising:
an IABP pump unit comprising a frame, a handle assembly comprising a handle, a pump disposed within the frame, a control unit configured to control the pump, a display device in electronic communication with the IABP, and a wheel assembly connected to the frame and operatively associated with the handle assembly,
wherein the wheel assembly of the IABP pump unit comprises a first and second wheel, each comprising an axel and an a respective axis having a fixed orientation with respect to the frame and movable between (i) a retracted position defining a first wheel track in which the wheels are spaced apart a predetermined distance and (ii) an extended position defining a second wheel track larger than the first wheel track in which the wheels are spaced apart a distance greater than the predetermined distance, the first and second wheels moving along their respective axis when alternating from the retracted position to the extended position; and
a wheeled cart, wherein the IABP pump unit is removably mountable to the cart, and wherein movement of the first and second wheels from the retracted position to the extended position is manually controlled by linear movement of at least a portion of the handle assembly from a first position to a second position, wherein the entirety of the handle in the second position is spaced apart from the entirety of the handle in its corresponding first position.

15. The intra-aortic balloon pump system of claim 14, wherein the cart is configured to removably and securely house and transport the IABP pump unit using at least one caster connected to the cart but without use of the first and second wheels, and wherein the IABP pump unit is also transportable independent from the cart via the first and second wheels when the IABP pump unit is removed from the cart.

16. The intra-aortic balloon pump system of claim 14, wherein the cart comprises a first power source used to power the IABP pump unit when the IABP pump unit is mounted on or in the cart, the IABP pump unit comprising a second power source used to power the IABP pump unit when the IABP pump unit is (i) removed from the cart or (ii) when the IABP pump unit is on or in the cart but the first power source is not functional.

17. The intra-aortic balloon pump system of claim 16, further comprising a third power source on the IABP pump unit, both the second power source and the third power source capable of powering the IABP pump unit independently when the IABP pump unit is removed from the cart.

18. The intra-aortic balloon pump system of claim 14, wherein the cart has a cavity comprising a bottom surface and one or more sidewalls extending vertically from the bottom surface, wherein the cavity is configured to receive with minimal clearance and at least partially encase the IABP pump unit through horizontal movement of the IABP pump unit into and out of the cavity.

19. The intra-aortic balloon pump system of claim 14, wherein the IABP pump unit has a first side shorter than two sides adjacent the first side, and wherein the first and second wheel of the IABP pump unit are mounted such that an axis of one of the first and second wheels is generally parallel to the first side and is at an elevation higher than an underside of the IABP pump unit.

20. The intra-aortic balloon pump system of claim 14, wherein the IABP pump unit has a front, a back, a top, a bottom, and two sides, the two sides have a horizontal width that is larger than the width of the back, wherein the common axis of the wheel assembly is located towards or at the bottom of the body and either adjacent to or in the proximity of the back, and wherein the first and second wheels are the only wheels directly connected to the IABP pump unit.

21. The intra-aortic balloon pump according to claim 14, wherein the frame has a bottom surface for resting on a ground surface, and an axis of one or both of the first and second wheel is located at an elevation higher than the frame's bottom surface.

22. A carrier configured for tilted wheel transport, comprising:
   a frame;
   a handle assembly connected to the frame and comprising a moveable handle grip; and
   a wheel assembly connected to the frame, wherein the wheel assembly comprises a first wheel and a second wheel, wherein each wheel is movable linearly between a retracted position defining a first wheel track in which the first and second wheels are spaced apart a predetermined distance and orientation, and an extended position defining a second wheel track larger than the first wheel track in which the wheels are spaced apart a distance greater than the predetermined distance yet have essentially the same predetermined orientation;
   wherein linear movement of the wheels from the retracted position to the extended position is manually controlled by linear movement of the handle grip from a first position to a second position, wherein the second position is linearly spaced apart from the first position and wherein the first wheel and the second wheel are located towards a vertical side of the frame and to accommodate tilted wheel support of the frame along a horizontal and flat surface when the frame is maintained in a tilted orientation with respect to the horizontal and flat surface and gripped at the handle grip by a user.

23. A cart comprising:
   an outer surface;
   a cavity disposed within the outer surface and comprising a bottom surface and one or more sidewalls extending vertically from the bottom surface; and
   a wheel arrangement coupled to the outer surface, wherein the cavity is dimensioned to receive the carrier of claim 22 so that the first wheel and the second wheel are contained within the carrier in the retracted position when the carrier is received by the cavity.

24. A method for enhancing the stability of a carrier for tilted wheel transport comprising a frame, a handle assembly connected to the frame and comprising a moveable handle grip, and a wheel assembly connected to the frame and to the handle assembly, the wheel assembly provides for an adjustable wheel track, wherein the wheel assembly comprises a first wheel and a second wheel, wherein each wheel is movable linearly between a retracted position defining a first wheel track in which the first and second wheels are spaced apart a predetermined distance and orientation, and an extended position defining a second wheel track larger than the first wheel track in which the wheels are spaced apart a distance greater than the predetermined distance and have essentially the same predetermined linear orientation; the method comprising the step of:
   moving the first wheel and the second wheel from (i) a retracted position defining a first wheel track in which the wheels are spaced apart a predetermined distance, to (ii) an extended position defining a second wheel track larger than the first in which the wheels are spaced apart a distance greater than the predetermined distance, and
   tilting the carrier onto the first wheel and the second wheel,
   wherein linear movement of the wheels from the retracted position to the extended position is manually controlled by linear movement of the handle grip from a first position to a second position, wherein the second position is linearly spaced apart from the first position, and
   wherein the first wheel and the second wheel are located towards a vertical side of the frame and to accommodate tilted wheel support of the frame along a horizontal and flat surface when the frame is maintained in a tilted orientation with respect to the horizontal and flat surface and gripped at the handle grip by a user.

25. The intra-aortic balloon pump system of claim 18, wherein the IABP pump unit comprises an internal helium reservoir disposed to supply helium gas to a pneumatic isolator, and the cart comprises a helium recharge tank that is connectable to replenish the internal helium reservoir with helium.

* * * * *